(12) United States Patent
Kyritsis

(10) Patent No.: US 7,931,142 B2
(45) Date of Patent: Apr. 26, 2011

(54) MEDICAL INSTRUMENT STERILIZATION POUCH

(76) Inventor: George Kyritsis, Laval (CA)

(\*) Notice: Subject to any disclaimer, the term of this patent is extended or adjusted under 35 U.S.C. 154(b) by 0 days.

(21) Appl. No.: 12/947,953

(22) Filed: Nov. 17, 2010

(65) Prior Publication Data

US 2011/0062038 A1  Mar. 17, 2011

Related U.S. Application Data

(63) Continuation-in-part of application No. 11/622,942, filed on Jan. 12, 2007, now Pat. No. 7,866,468.

(51) Int. Cl.
*B65D 83/10* (2006.01)

(52) U.S. Cl. .................. 206/363; 206/440; 206/484.1

(58) Field of Classification Search ............... 206/484.1, 206/484, 484.2, 438, 439, 363, 364, 365, 206/524.1, 524.3, 524.6; 493/186, 189, 199, 493/227

See application file for complete search history.

(56) References Cited

U.S. PATENT DOCUMENTS

| | | | | |
|---|---|---|---|---|
| 4,511,035 A | * | 4/1985 | Alpern | 206/363 |
| 5,217,772 A | * | 6/1993 | Brown et al. | 428/41.3 |
| 6,098,800 A | * | 8/2000 | Bennish et al. | 206/439 |
| 6,594,971 B1 | * | 7/2003 | Addy et al. | 53/413 |
| 2006/0240203 A1 | * | 10/2006 | Matsumoto et al. | 428/35.2 |

\* cited by examiner

*Primary Examiner* — Jacob K Ackun, Jr.
(74) *Attorney, Agent, or Firm* — Neustel Law Offices

(57) ABSTRACT

The sterilization pouch includes a sealable inner space for receiving one or more medical instruments, a preferred instrument being hinged pliers. The pouch is generally comprised of first and second layers, the layers being sealed around a peripheral edge except a separation in the seal to form an opening for accessing the inner space and a flap for closing the opening. The pouch has an upper portion and a first and second lower portion extending therefrom, the upper portion being comprised of a vertical length just as long or longer than the lower portions to allow for insertion and removal of the instrument through the opening, wherein the opening is along the peripheral edge of the upper portion. A recessed portion separates the first and second lower portions, such as to permit the inner space to connect the first and second lower portions only through the upper portion.

20 Claims, 25 Drawing Sheets

MEDICAL INSTRUMENT STERILIZATION POUCH

CROSS REFERENCE TO RELATED APPLICATIONS

I hereby claim benefit under Title 35, United States Code, Section 120 of U.S. patent application Ser. No. 11/622,942 filed Jan. 12, 2007 now U.S. Pat. No. 7,866,468. This application is a continuation-in-part of the Ser. No. 11/622,942 application. The Ser. No. 11/622,942 application is currently pending. The Ser. No. 11/622,942 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to sterilization pouches and more specifically it relates to a medical instrument sterilization pouch for efficiently bagging hinged instruments.

2. Description of the Related Art

Any discussion of the related art throughout the specification should in no way be considered as an admission that such related art is widely known or forms part of common general knowledge in the field.

Sterilization pouches have been in use for years. Typically, when in a medical, dental or other similar environment it is necessary to keep all the instruments in pouches prior to use. The pouches effectively serve to prevent germs or other harmful toxins from coming in contact with the instruments when the instruments are not being used. The instruments are also generally sterilized prior to being inserted into the pouch or sterilized while inserted within the pouch.

Sterilization pouches are manufactured from many different materials, sizes and with many different sealing mechanisms. Although, one universal feature that generally exists in all sterilization pouches is that the sterilization pouches are generally rectangular in shape. This poses a problem with respect to hinged instruments, such as but not limited to orthodontic pliers and surgical pliers in that the hinged instruments cannot adequately fit on their respective tool racks (i.e. pliers rack) once the hinged instruments are in the pouch.

Because of the general lack of efficiency and practicality in the prior art there is the need for a new and improved medical instrument sterilization pouch for efficiently bagging hinged instruments.

BRIEF SUMMARY OF THE INVENTION

The general purpose of the present invention is to provide a medical instrument sterilization pouch that has many of the advantages of the sterilization pouches mentioned heretofore. The invention generally relates to a sterilization pouch which includes first and second layers, the layers being sealed around a peripheral edge except a separation in the seal to form an opening for accessing the inner space and a flap for closing the opening. The pouch has an upper portion and a first and second lower portion extending therefrom, the upper portion being comprised of a vertical length just as long or longer than the lower portions to allow for insertion and removal of the instrument through the opening, wherein the opening is along the peripheral edge of the upper portion. A recessed portion separates the first and second lower portions, such as to permit the inner space to connect the first and second lower portions only through the upper portion.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide a medical instrument sterilization pouch for efficiently bagging hinged instruments.

An object is to provide a medical instrument sterilization pouch that has an elongated upper portion generally at least as long or longer than the respective lower portions.

An object is to provide a medical instrument sterilization pouch that allows for aseptic delivery of a medical instrument.

Another object is to provide a medical instrument sterilization pouch that accommodates a variety of different style hinged instruments.

An additional object is to provide a medical instrument sterilization pouch that may be utilized with non-hinged instruments.

A further object is to provide a medical instrument sterilization pouch that allows the hinged instruments to be placed on their respective holding racks (i.e. pliers rack) after the hinged instruments are bagged.

Another object is to provide a medical instrument sterilization pouch that includes a durable outer material to prevent puncture by the instrument.

Another object is to provide a medical instrument sterilization pouch that mimics the shape and size of the medical instruments utilized thus producing less environmental and biological waste.

Another object is to provide a medical instrument sterilization pouch that has an internal chemical indicator which changes color during sterilization of the medical instrument sealed within the pouch.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
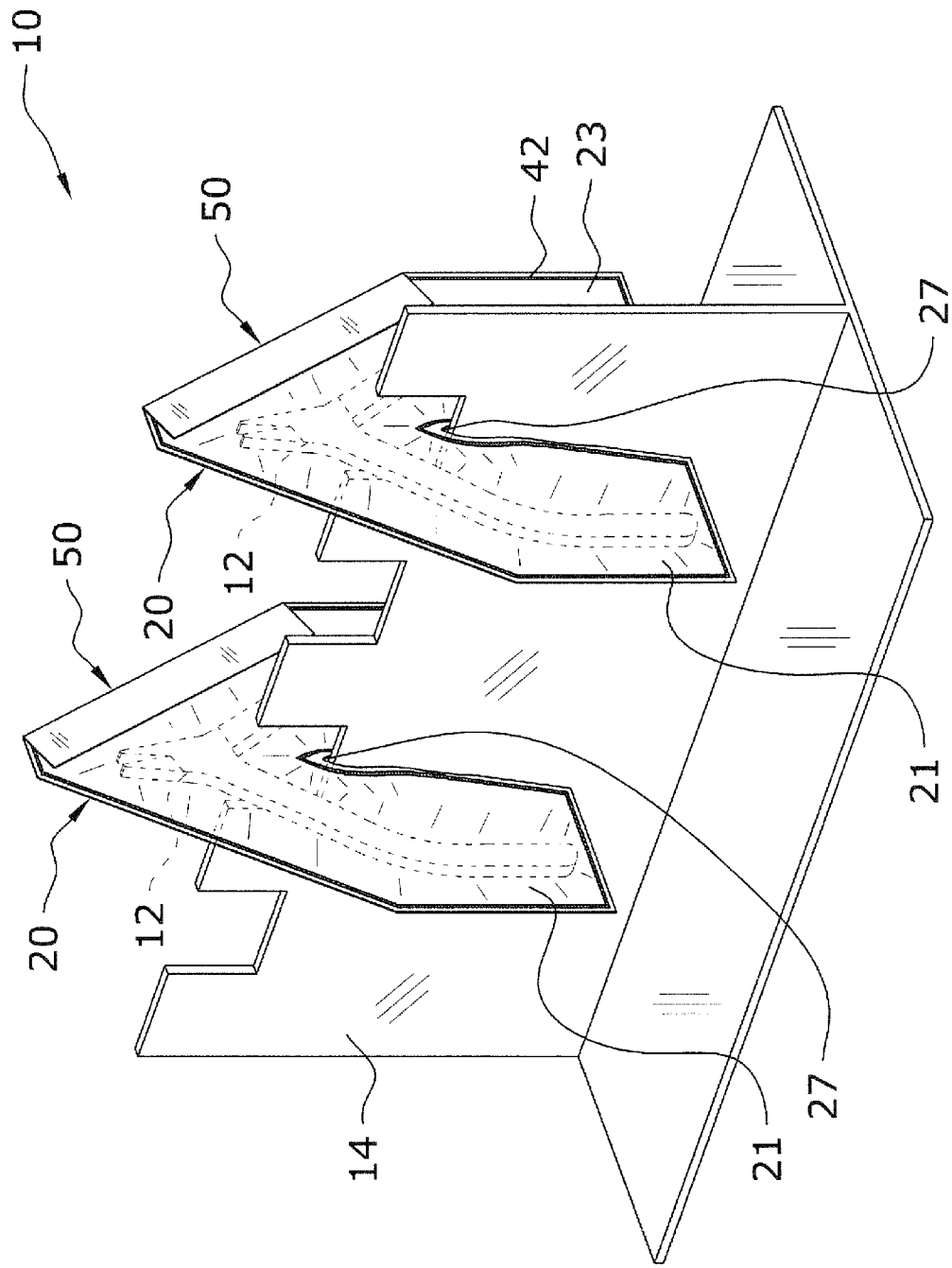
FIG. 1 is an upper perspective view of the present invention in use and positioned upon a tool rack.

Turning now descriptively to the drawings, in which similar reference characters denote similar elements throughout the several views, FIGS. 1 through 25 illustrate a medical instrument and sterilization pouch system 10, which comprises a pouch 20 including a first layer 30 and a second layer 40, wherein the first layer 30 and/or the second layer 40 are comprised of a gas permeable material and wherein the first layer 30 is attached to the second layer 40 via an outer seal 42 substantially surrounding an outer perimeter of the first layer 30 and the second layer 40. The layers 30, 40 are sealed around a peripheral edge except a separation in the seal 42 to form an opening 29 for accessing the inner space and a flap 50 for closing the opening 29.

The pouch 20 includes a first lower portion 21 and a second lower portion 23, wherein the first lower portion 21 is separated from the second lower portion 23 and wherein the first lower portion 21 and the second lower portion 23 form a recessed portion 27 between thereof. The upper portion 25 is comprised of a vertical length just as long or longer than the lower portions 21, 23 to allow for insertion and removal of the instrument 12 through the opening 29, wherein the opening 29 is along the peripheral edge of the upper portion 25. The pouch 20 preferably receives a medical instrument 12 (e.g. surgical pliers), wherein the medical instrument 12 is sterilized within the pouch 20 and is then positioned upon a respective tool rack 14 (i.e. pliers rack).

The pouch 20 is preferably comprised of a configuration to hold hinged medical instruments 12, such as but not limited to orthodontic pliers, surgical pliers, tweezers and scissors. The pouch 20 also preferably adequately holds non-hinged medical instruments 12, such as but not limited to inspection mirrors, dental picks, dental scalers and spatulas, wherein the non-hinged medical instruments 12 are simply inserted into the pouch 20 in a crossed manner. It is also appreciated that the pouch 20 may hold various other tools or equipment not associated with medical use. The pouch 20 preferably mimics the shape of the medical instrument 12, thus requiring the minimal amount of packaging for each medical instrument 12.

Figure 6:
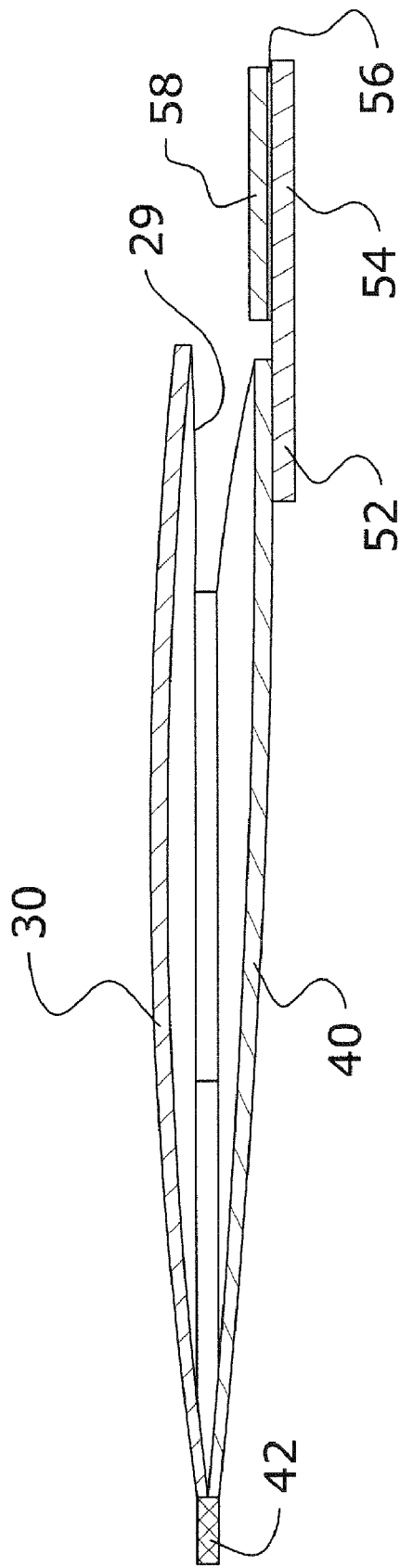
FIG. 6 is a sectional view taken along lines 6-6 of FIG. 2.

The pouch 20 includes a first layer 30 and a second layer 40 as shown in FIG. 6. The first layer 30 and the second layer 40 are preferably both comprised of a gas permeable material. The first layer 30 and the second layer 40 are further impermeable to micro-organisms or toxins. The first layer 30 and the second layer 40 are further preferably comprised of a material resistant enough to withstand both steam and dry heat sterilization cycles. The first layer 30 and the second layer 40 may further be comprised of various materials, such as but not limited to nylon films, polypropylene films, polyethylene films, polyester polypropylene pellicles, blends of medical grade paper or a combination of two or more materials. The first layer 30 and the second layer 40 are further preferably comprised of a transparent material so as to easily view the medical instrument 12 within the pouch 20. The first layer 30 and the second layer 40 may also include chemical, steam and heat activated indicators. The indicators are preferably painted on the first layer 30 or the second layer 40.

The first layer 30 and the second layer 40 may be comprised of a plurality of different shapes and sizes, wherein each of the configurations of the first layer 30 and the second layer 40 forms a recessed portion 27 to receive the legs of a medical instrument 12 as illustrated in FIGS. 1 through 17. The first layer 30 and the second layer 40 are further preferably comprised of substantially similar configurations.

The first layer 30 and the second layer 40 are preferably attached substantially near an outer perimeter of the first layer 30 and the second layer 40 via an outer seal 42 as shown in FIGS. 1 through 5. The outer seal 42 extends substantially across an entire perimeter of the first layer 30 and the second layer 40, wherein the outer seal 42 leaves room for an opening 29 along at least one outer edge to access the inner space between the first layer 30 and the second layer 40.

The pouch 20 includes the first lower portion 21, the second lower portion 23 and the upper portion 25 opposite the first lower portion 21 and the second lower portion 23. The first lower portion 21 and the second lower portion 23 are preferably separably formed, wherein each lower portion preferably receives a respective leg of a medical instrument 12. In the case of the medical instrument 12 being comprised of a medical, hinged pliers, the head of the pliers 12 is received by the upper portion 25, the first leg of the pliers 12 is received by the first lower portion 21, and the second leg of the pliers 12 is received by the second lower portion 23 as illustrated in FIGS. 1 and 3-5.

The recessed portion 27 is formed between the first lower portion 21 and the second lower portion 23 as shown in FIGS. 1 through 5. The recessed portion 27 is preferably positioned upon a respective tool rack 14 (i.e. pliers rack) when storing or sterilizing the medical instrument 12 (i.e. surgical pliers) within the pouch 20 as illustrated in FIG. 1. Sterilizing the surgical pliers or other hinged instruments 12 upon the pliers rack 14 prevents the pouches 20 from being stacked upon one another, wherein stacking multiple medical instruments 12 upon one another may prevent the sterilization substance from coming in contact with the entire medical instrument 12. Utilizing the tool rack 14 allows the pouches 20 to be spaced adequately apart and thus allows the sterilization substance to effectively contact all surfaces of the medical instrument 12.

Figure 14:
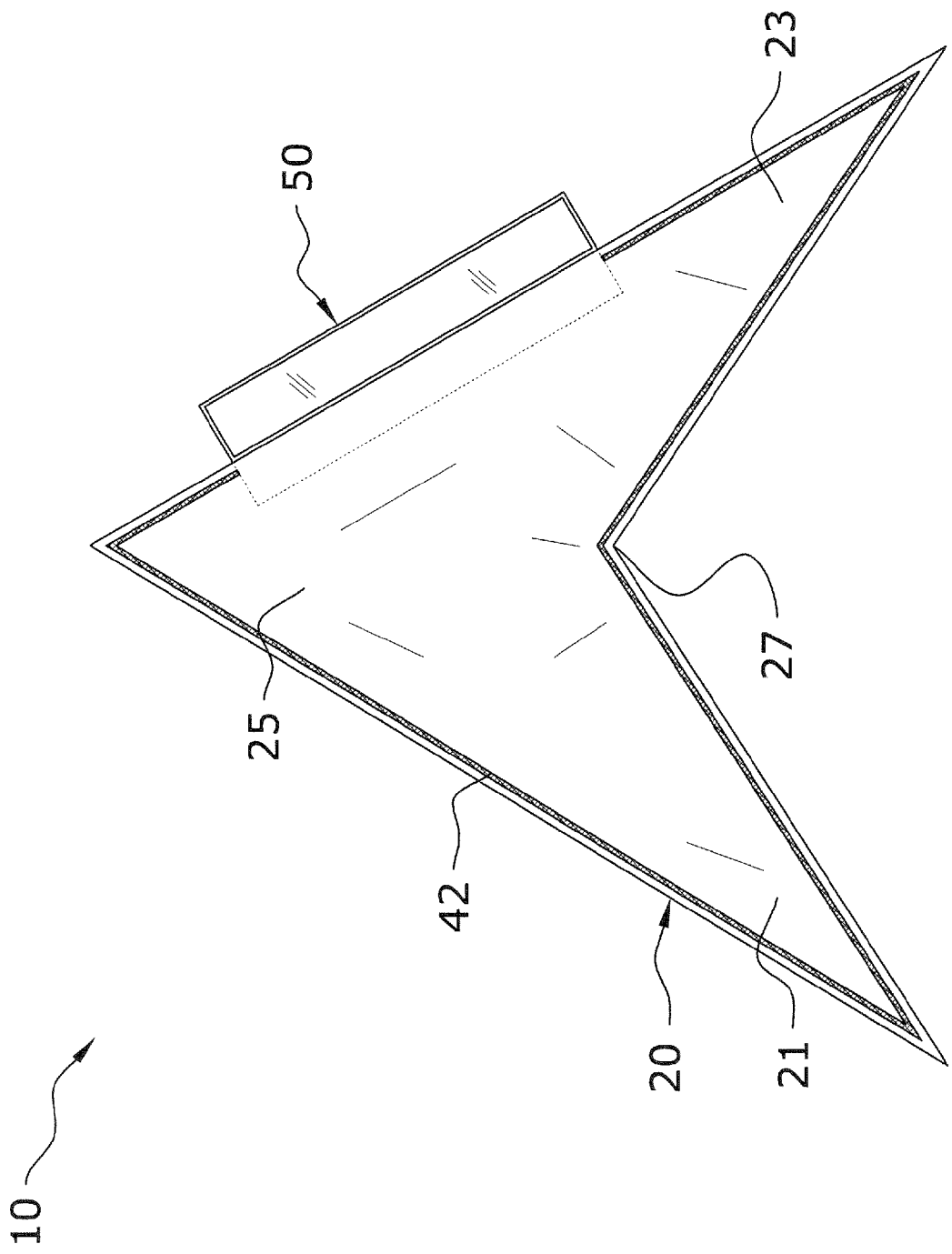
FIG. 14 is a front view of a fourth alternative embodiment of the present invention.
Figure 15:
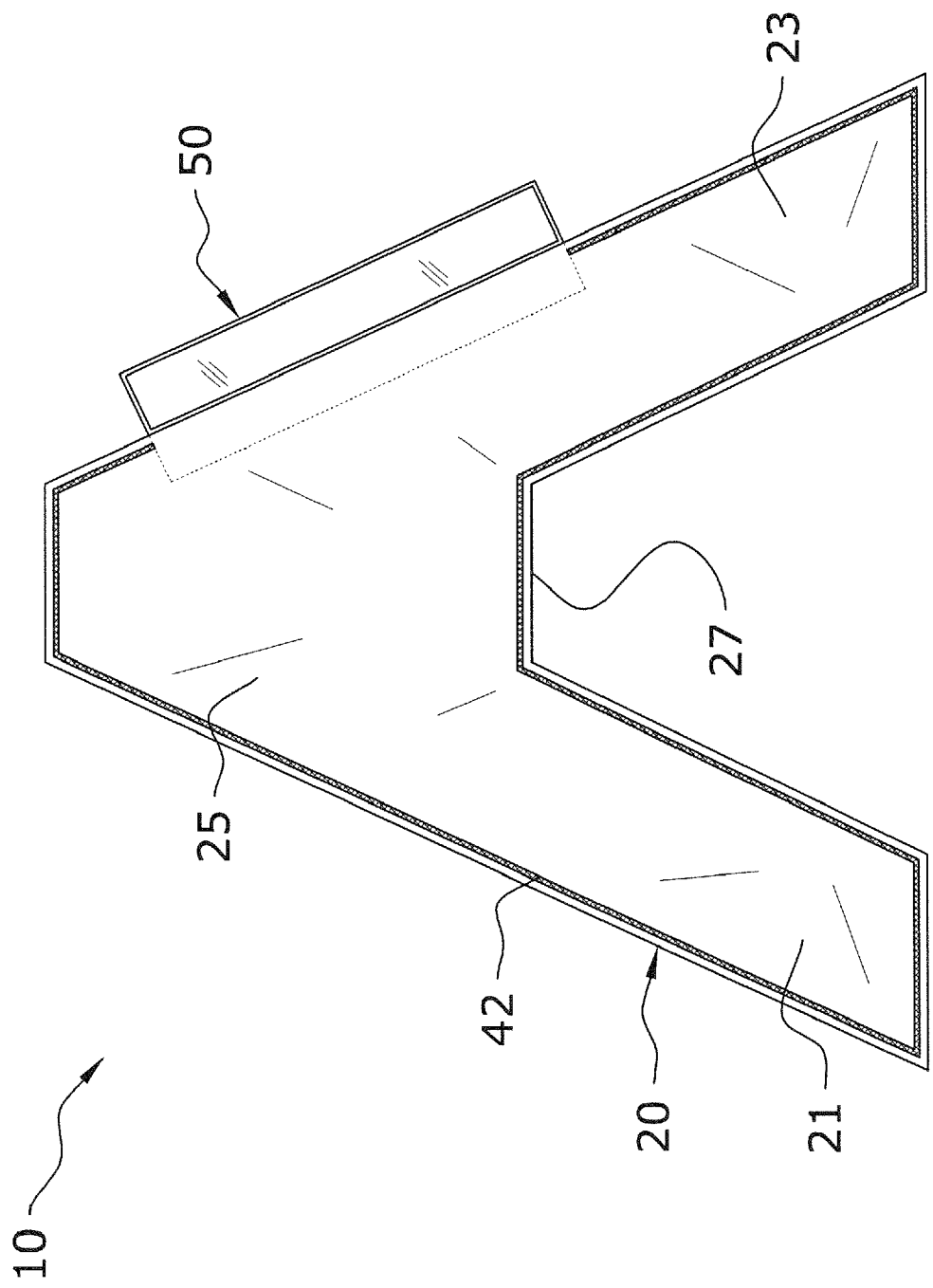
FIG. 15 is a front view of a fifth alternative embodiment of the present invention.
Figure 16:
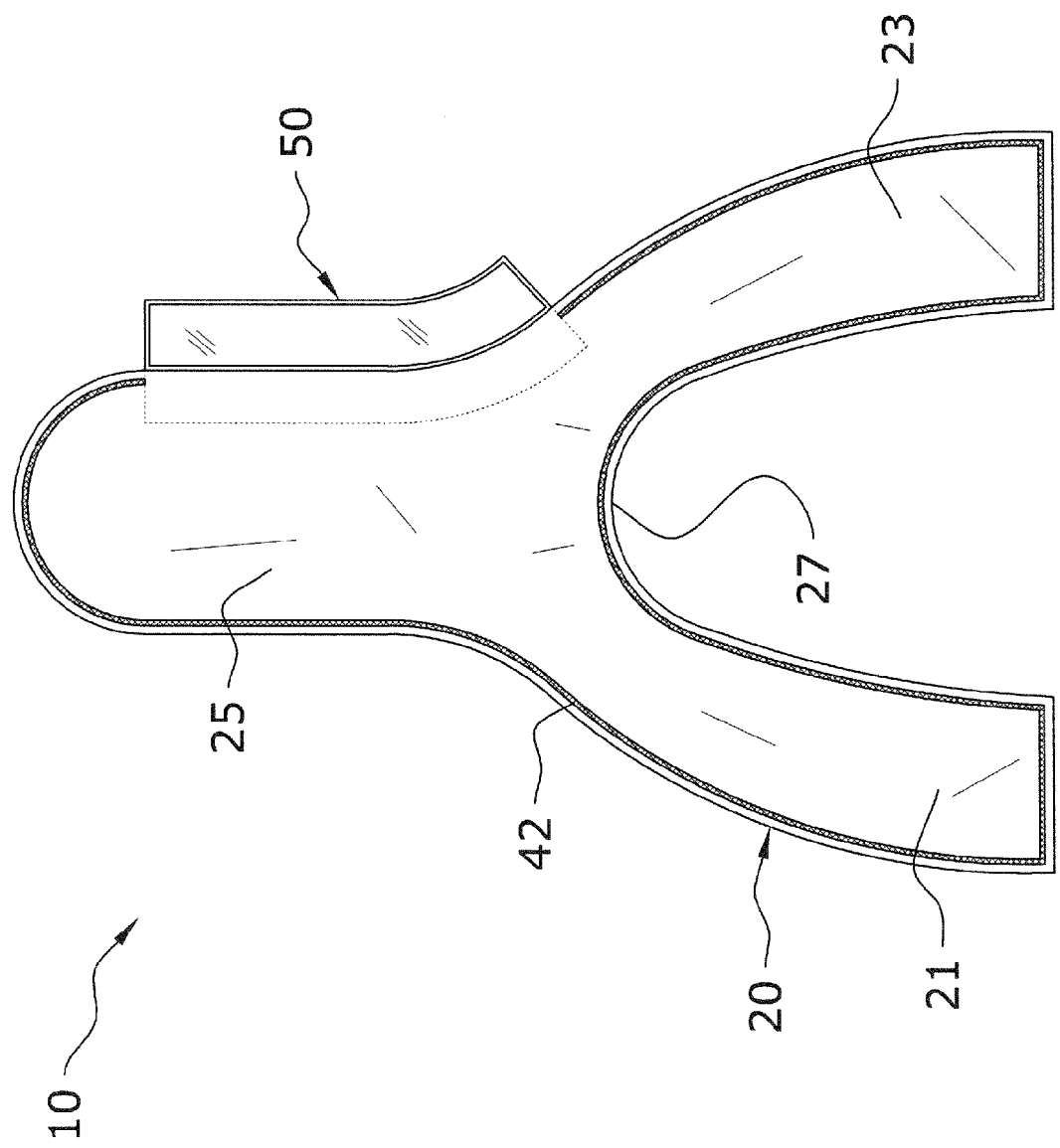
FIG. 16 is a front view of a sixth alternative embodiment of the present invention.
Figure 17:
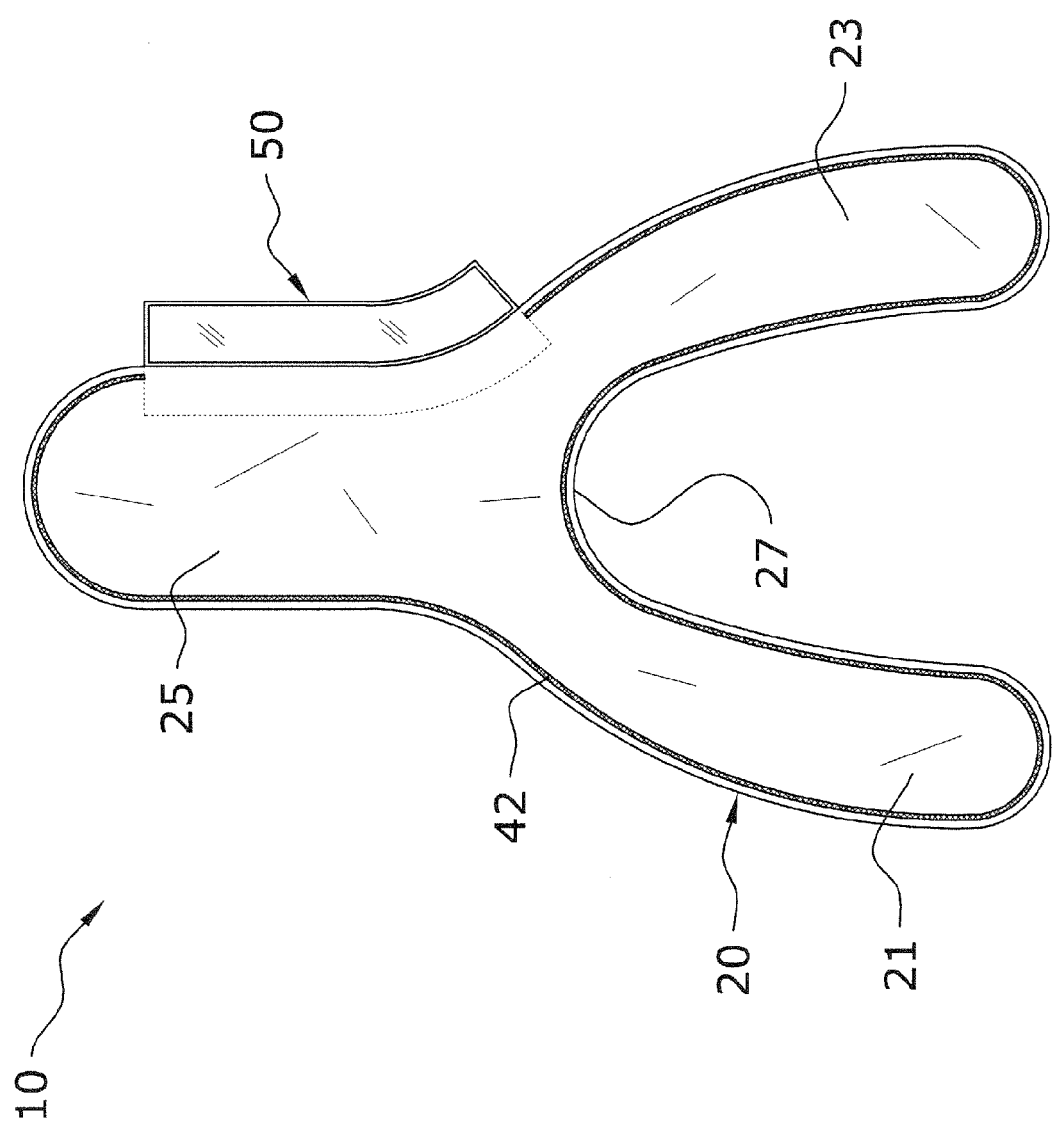
FIG. 17 is a front view of a seventh alternative embodiment of the present invention.

The recessed portion 27 is preferably comprised of a triangular shaped configuration. An apex of the recessed portion 27 preferably extends upwardly toward the upper portion 25 as shown in FIGS. 1 through 5. It is appreciated that the recessed portion 27 may also be comprised of a substantially semi-circular or oval shaped configuration as illustrated in FIGS. 16 and 17, or may have a flat upper edge as illustrated in FIG. 15. It is further appreciated that the recessed portion 27 may be comprised of a plurality of various configurations all which substantially separate the first lower portion 21 from the second lower portion 23 as illustrated in FIGS. 11 through 15. The recessed portion 27 is adapted to permit the inner space to connect the first lower portion 21 and the second lower portion 23 through the upper portion 25 and to restrict the inner space from connecting the first lower portion 21 directly to the second lower portion 23.

Figure 2:
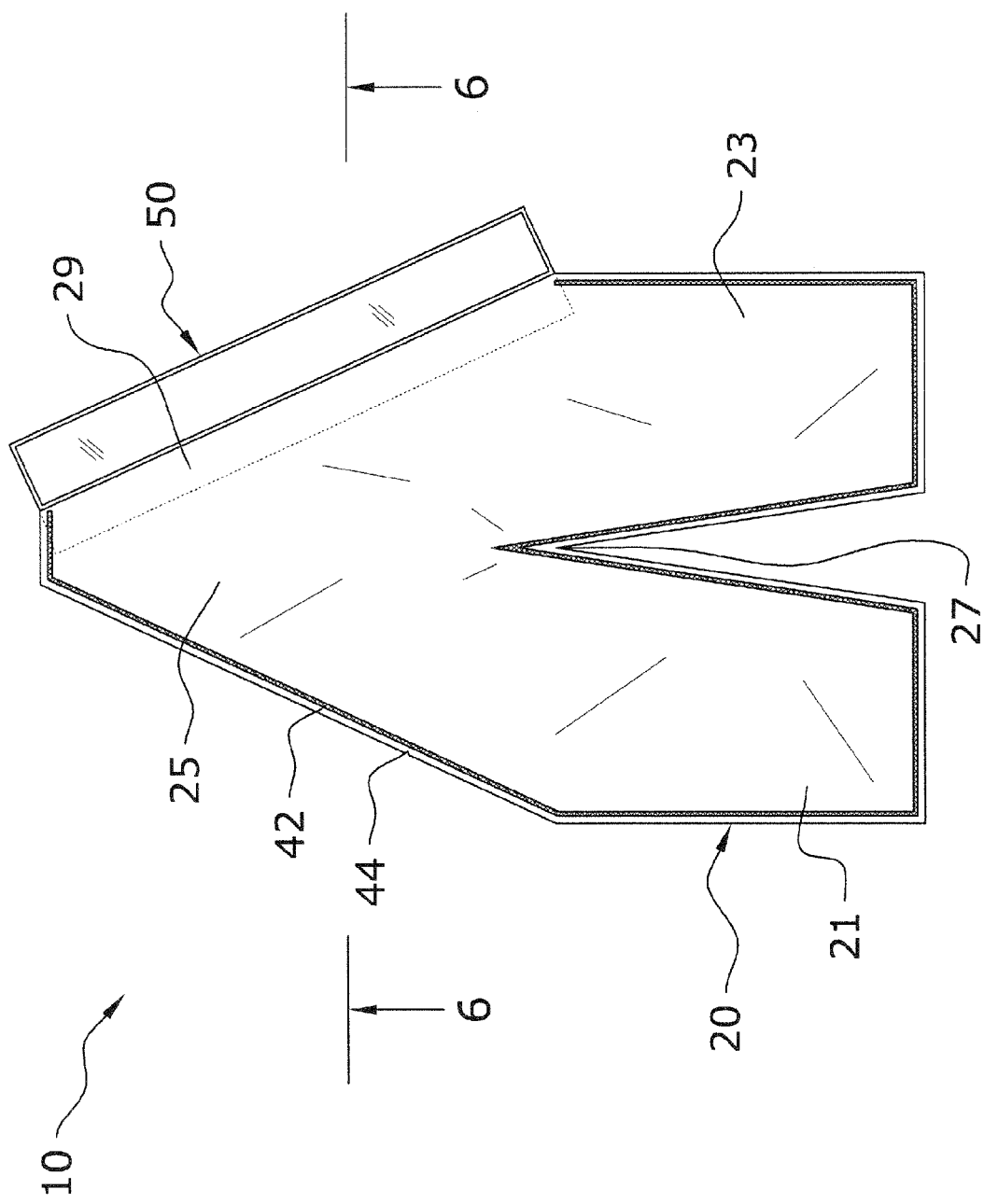
FIG. 2 is a front view of the present invention.
Figure 3:
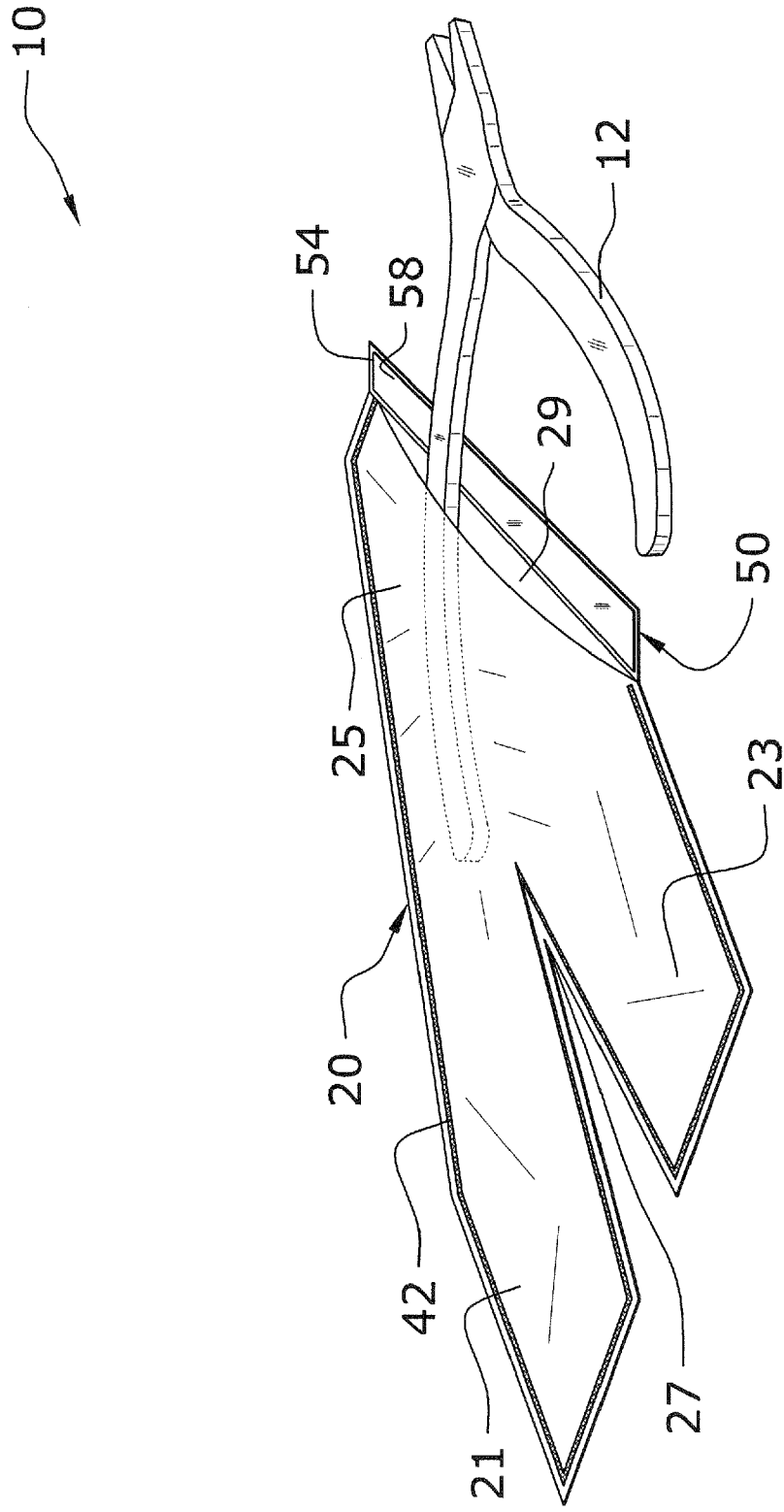
FIG. 3 is an upper perspective view of the present invention with a medical instrument partially inserted within the pouch.

The first lower portion 21 and the second lower portion 23 preferably substantially mirror each other as shown in FIG. 2. The ends of the first lower portion 21 and the second lower portion 23 may also be comprised of a plurality of configurations, such as but not limited to flat, inclined or rounded as illustrated in FIGS. 2 and 11 through 17.

Figure 4:
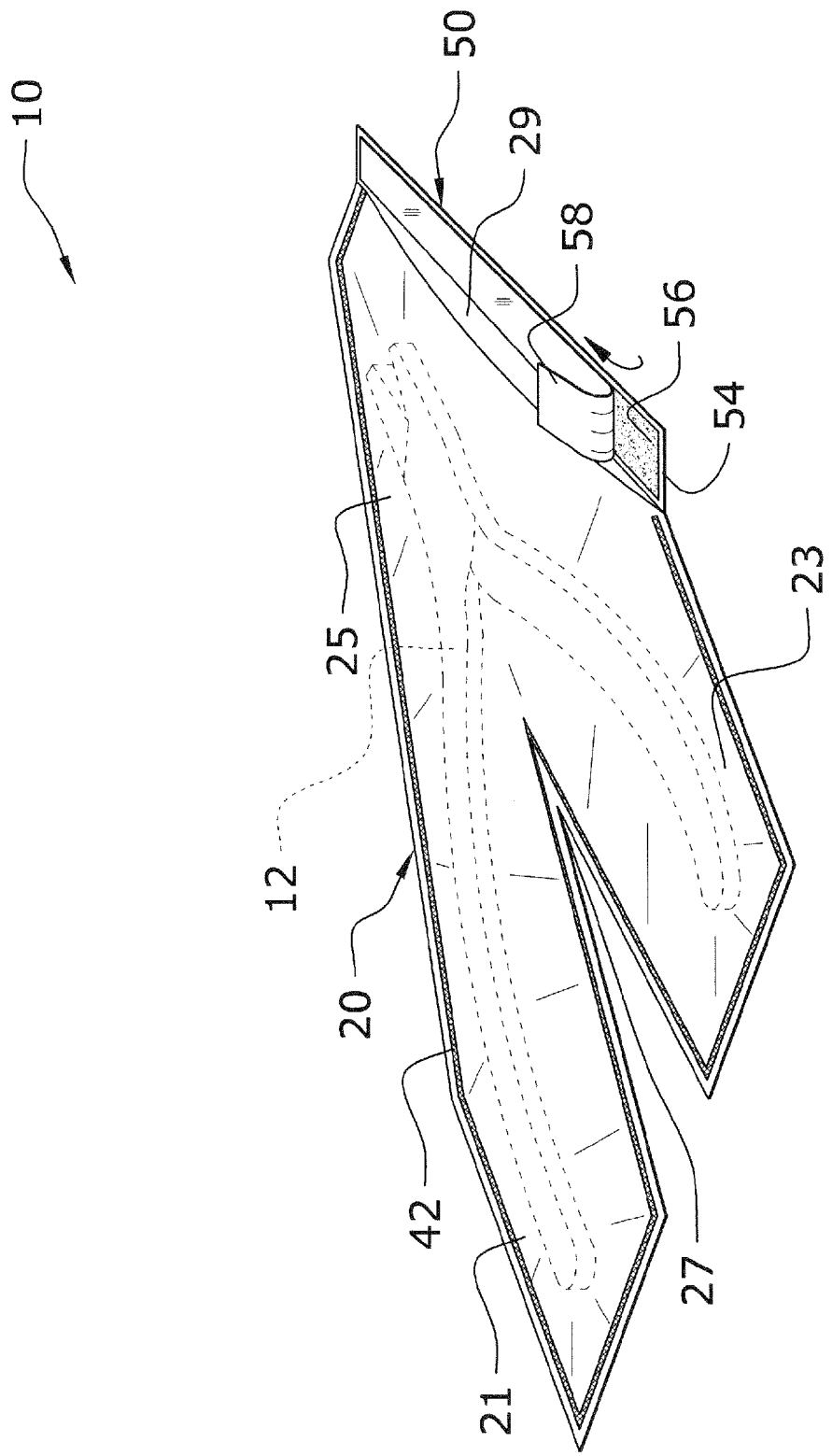
FIG. 4 is an upper perspective view of the present invention with a medical instrument inserted within the pouch.
Figure 5:
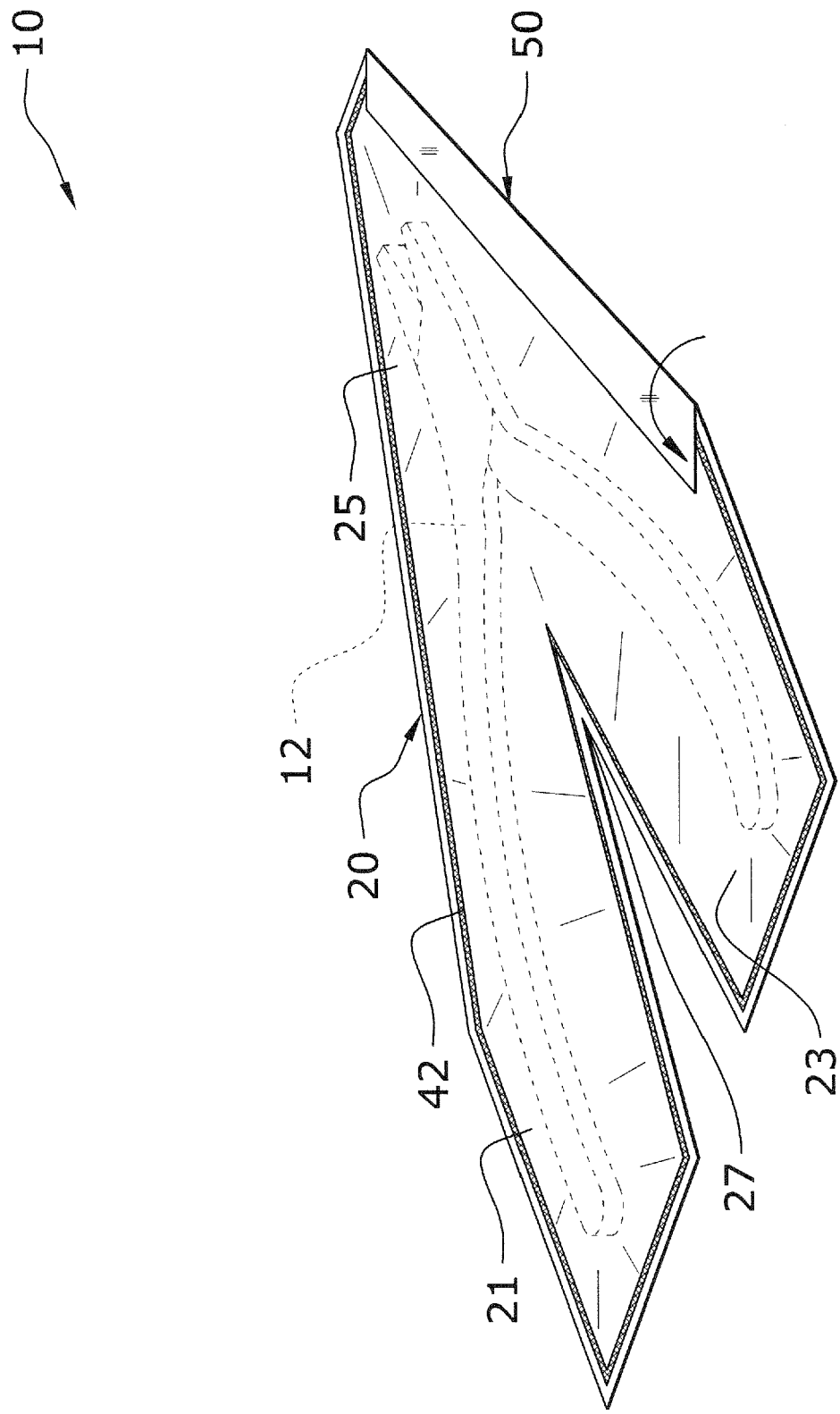
FIG. 5 is an upper perspective view of the present invention with a medical instrument inserted within the pouch and the flap sealed upon the pouch.
Figure 8:
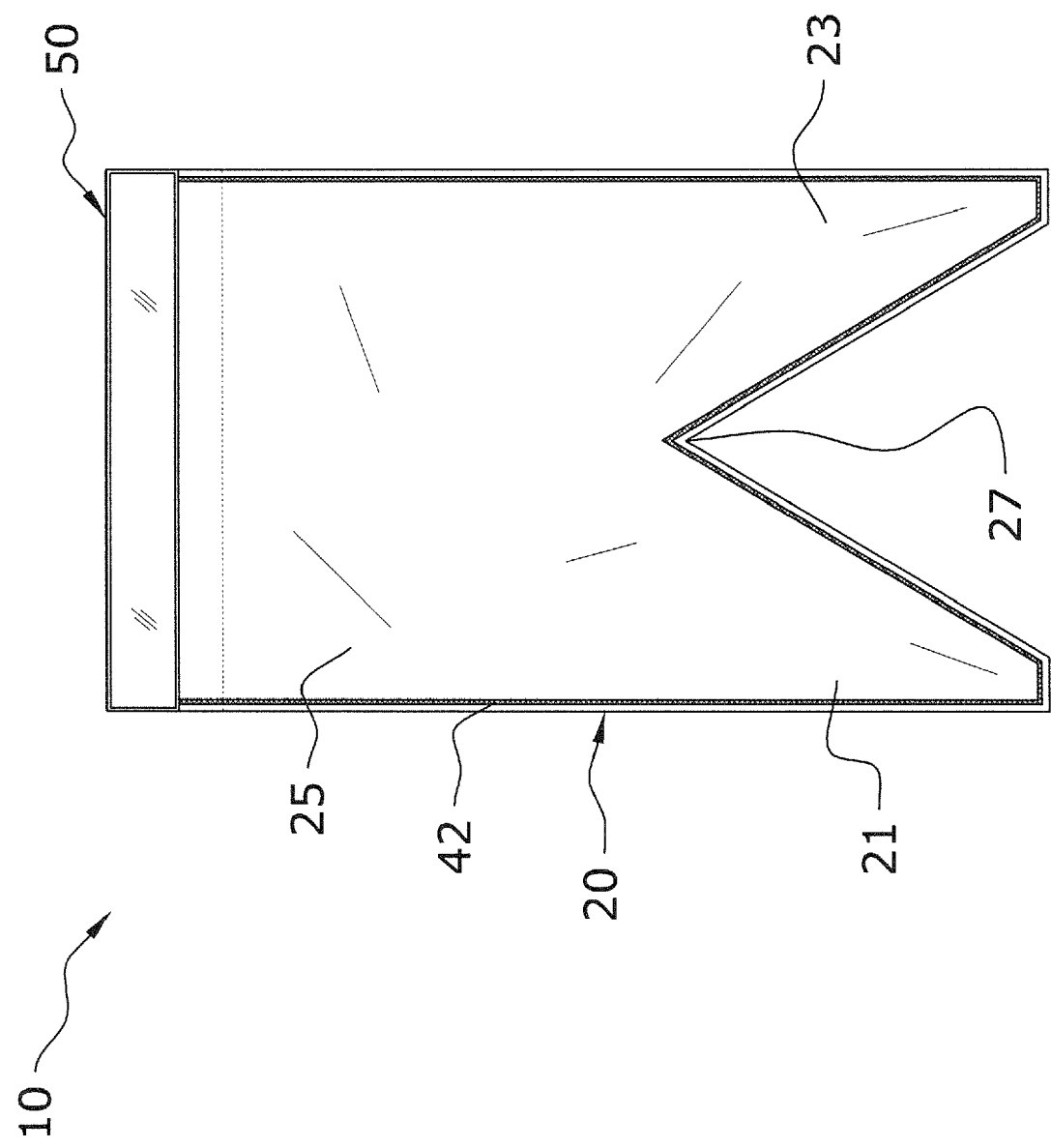
FIG. 8 is a front view of a pouch illustrating a second step in the first example of manufacturing the present invention.

The upper portion 25 extends upwardly from lower portions 21, 23 and preferably receives the head of the medical instruments 12 as illustrated in FIGS. 1, 4 and 5. The upper portion 25 may also be comprised of a plurality of configurations, as illustrated in FIGS. 11 through 17. The upper portion 25 may include at least one tapered edge or a bottle neck configuration to better conform to the overall shape of the medical instrument 12 as illustrated in FIG. 2. The inside of the pouch 20 is preferably fluidly connected from the first lower portion 21 to the upper portion 25 to the second lower portion 23. The inside of the first lower portion 21 is preferably substantially fluidly sealed from the inside of the second lower portion 23 via the recessed portion 27. The upper portion 25 may be triangular shaped such as illustrated in FIGS. 2 and 14, rectangular shaped such as illustrated in FIG. 8, or be comprised of other polygonal or curved shapes, such as illustrated in FIGS. 13 and 15-17.

The opening 29 is preferably formed along at least one edge of the upper portion 25 of the pouch 20 as shown in FIGS. 1 through 5, wherein the outer seal 42 does not extend across the perimeter of the first layer 30 and the second layer 40 along the opening 29. The opening 29 is further preferably positioned along a tapered, angular end of the upper portion 25 as illustrated in FIGS. 1 through 5. The opening 29 allows access to the inside of the pouch 20 between the first layer 30 and the second layer 40. The opening 29 is also preferably large enough to allow the hinged instrument to be inserted adequately into the pouch 20. The opening 29 may also be formed along the top edge of the upper portion 25, such as in the rectangular embodiment of FIG. 8 and thus be oriented horizontally.

The vertical length of the upper portion 25 is also preferably just as long or longer than the first lower portion 21 and also just as long or longer than the second lower portion 23 thus being able to adequately permit insertion of the medical instrument 12 within the pouch 20 through the opening 29 of the upper portion 25. Further, in some embodiments, the upper portion 25 is longer than the first lower portion 21 and is longer than the second lower portion 23. For example, the embodiment of the pouch 20 in FIG. 8 clearly illustrates that the upper portion 25 is longer in length than the first lower portion 21 and the second lower portion 23. The upper portion 25 is also illustrated as just as long or longer than the lower portions 21, 23 in FIGS. 2 and 11 through 17.

The flap 50 covers the opening 29 after the medical instrument 12 has been inserted within the pouch 20 to prevent contaminants and toxins from coming into contact with the medical instrument 12. The flap 50 preferably extends along an entire length of the opening 29 as shown in FIGS. 1 through 5, wherein the opening 29 extends along an edge of the upper portion 25. The flap 50 is further preferably parallel with the opening 29 and thus may extend along an angular edge as illustrated in FIG. 2, a horizontal edge as illustrated in FIG. 8, or partially along a vertical edge as illustrated in FIGS. 16 and 17.

The flap 50 includes a first flange portion 52 and a second flange portion 54. The first flange portion 52 is preferably attached to the upper portion 25 and is substantially parallel with the opening 29. The second flange portion 54 preferably extends outwardly from the first flange portion 52 as shown in FIG. 6. The second flange portion 54 further preferably extends outwardly from the upper portion 25. The second flange portion 54 is also preferably parallel with the opening 29 as illustrated in FIG. 6.

The second flange portion 54 preferably includes a sealing member 56 extending across a longitudinal axis of the second flange portion 54 as shown in FIG. 4. The sealing member 56 is positioned about an upper side of the second flange portion 54 of the flap 50. The sealing member 56 is further preferably comprised of an adhesive material so as to adequately stick to the upper side of the first layer 30. An outer layer 58 is preferably removably attached to the upper side of the sealing member 56 to prevent foreign substances from attaching to the sealing member 56 when not in use.

The sealing member 56 and the outer layer 58 function in a similar manner to a sticker, wherein the backing of the sticker must be removed to attach the sticky surface to an object. It is appreciated that the opening 29 of the pouch 20 may be sealed utilizing a plurality of various manners rather than the preferred method, such as but not limited to a self-sealing extremity or a thermo-sealing blade.

Figure 7:
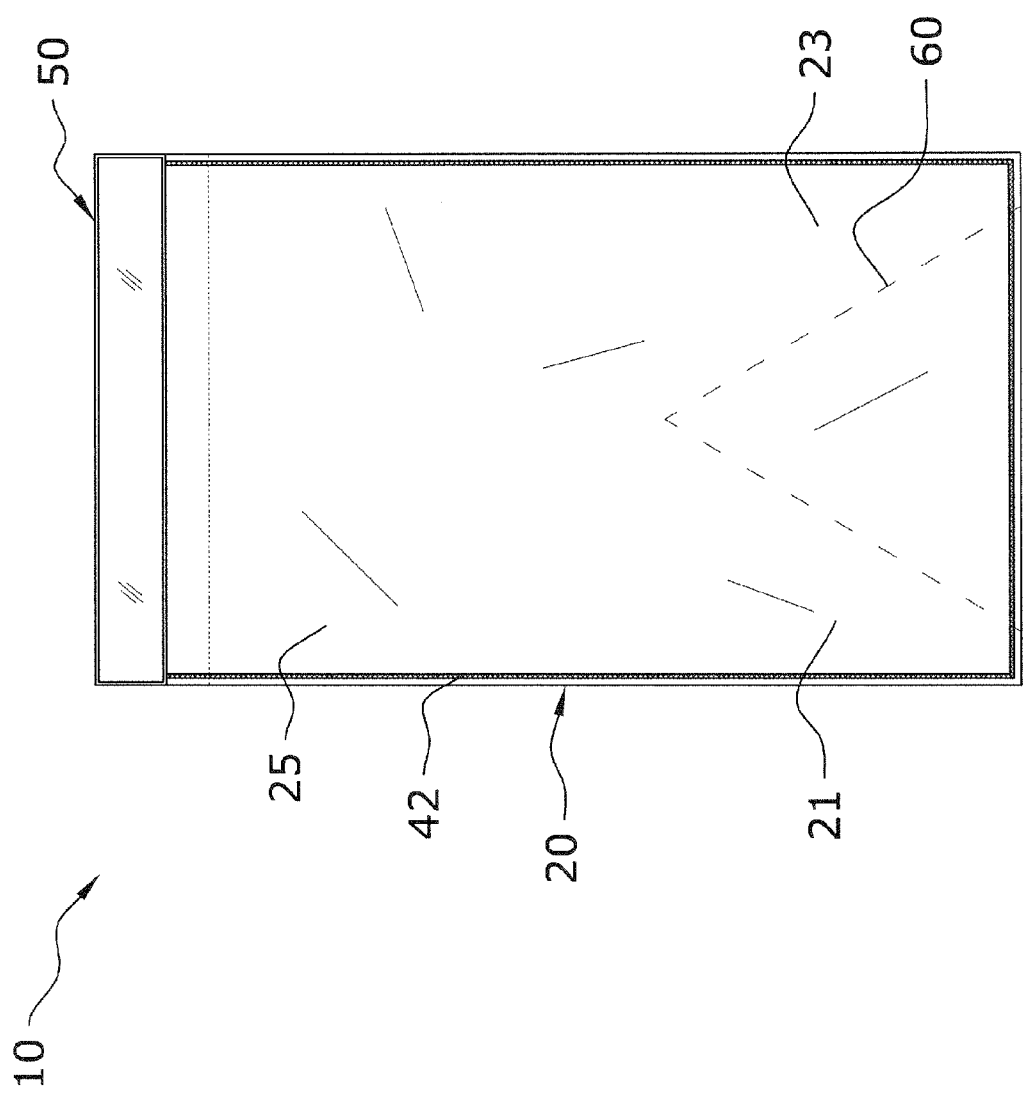
FIG. 7 is a front view of a pouch illustrating a first step in a first example of manufacturing the present invention.

The present invention may be manufactured in various manners as illustrated in FIGS. 7 through 11. A first example of a way to manufacture the present invention involves utilizing a standard rectangular pouch 20 as illustrated in FIGS. 7 and 8. A wedge is cut out of the pouch 20 from a substantially center bottom edge of the pouch 20 as illustrated by the cutting line 60 in FIG. 7. The wedge is preferably comprised of a substantially triangular shaped configuration. The wedge is then removed from the bottom of the pouch 20, thus forming a first lower portion 21, a second lower portion 23 and a recessed portion 27 between thereof. The perimeter of the recessed portion 27 is then sealed to prevent any microorganisms or toxins from entering the inside of the pouch 20 via the recessed portion 27.

Figure 9:
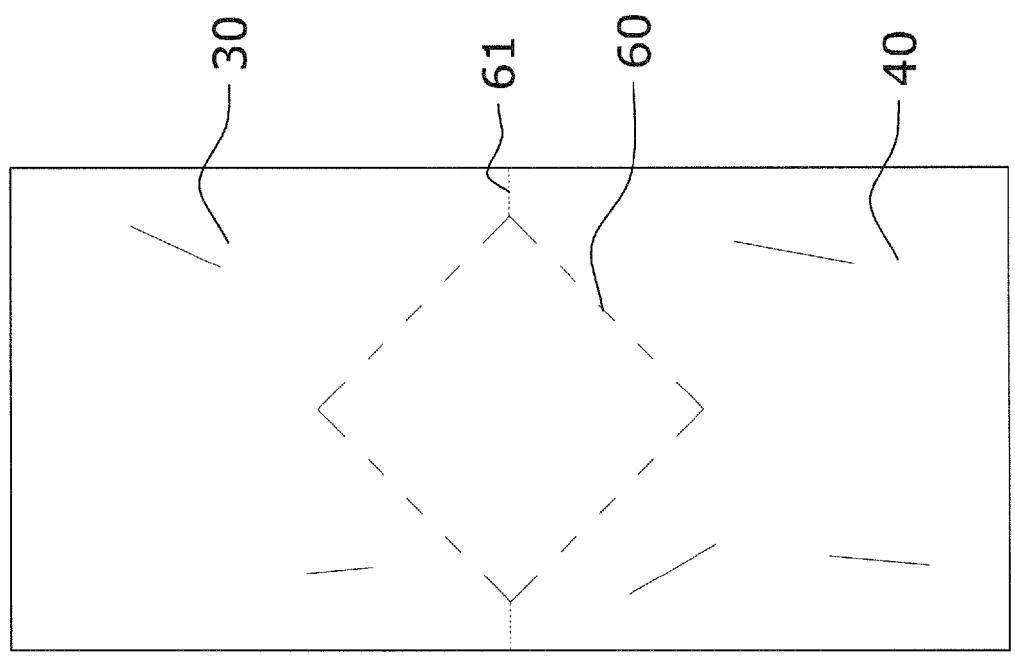
FIG. 9 is a front view of a pouch illustrating a first step in a second example of manufacturing the present invention.
Figure 10:
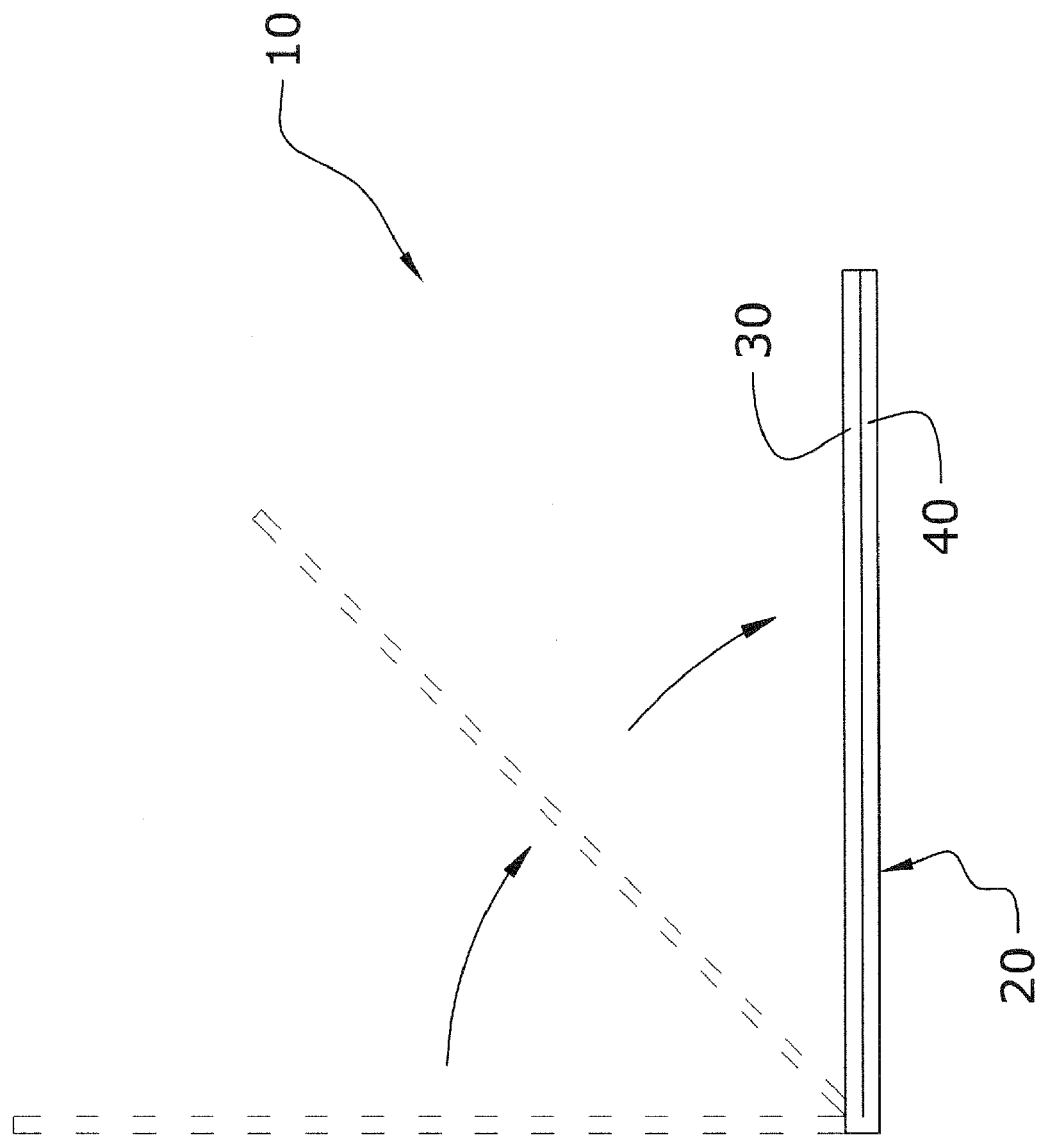
FIG. 10 is a front view of a pouch illustrating a second step in the second example of manufacturing the present invention.
Figure 11:
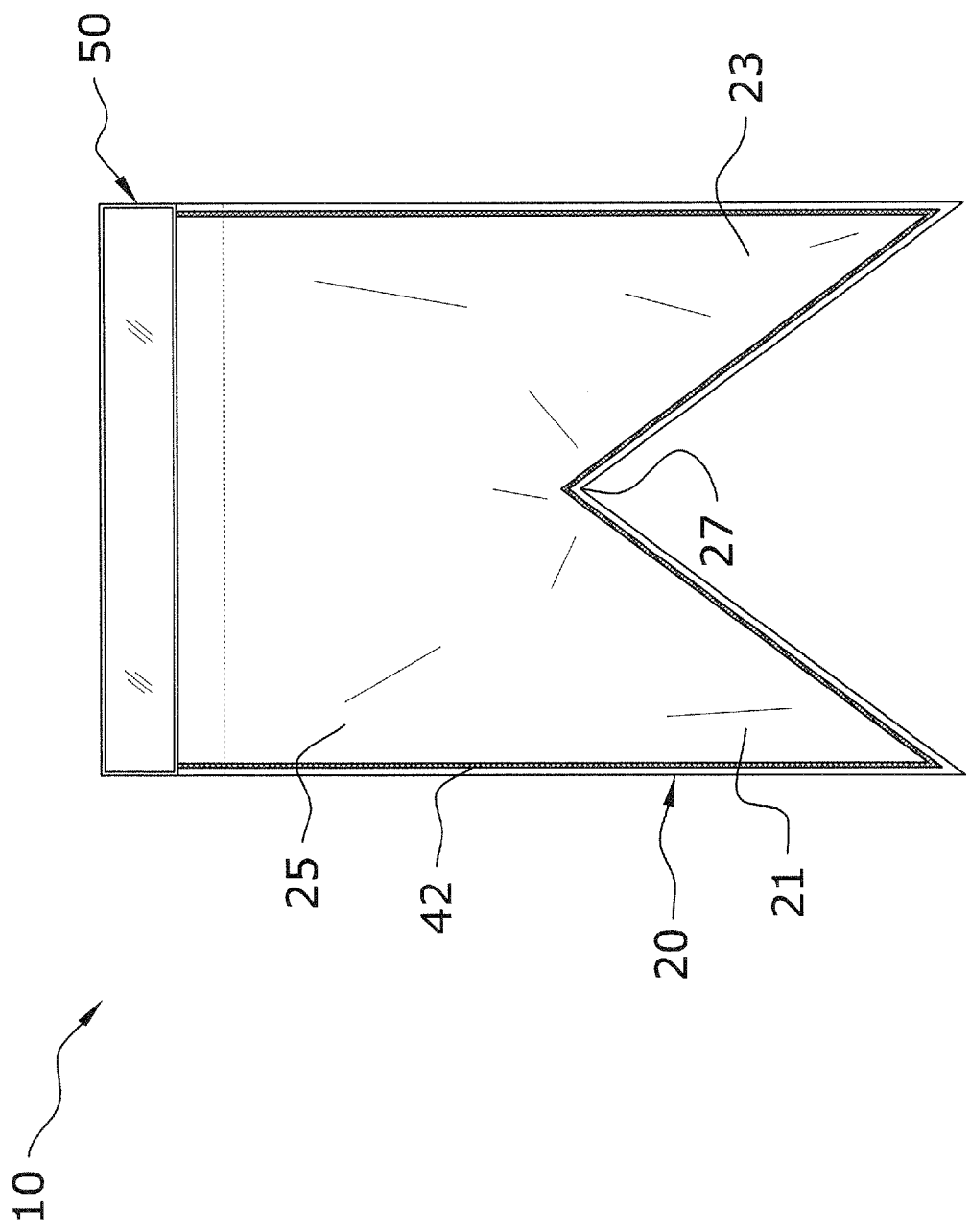
FIG. 11 is a front view of a first alternative embodiment of the present invention.
Figure 12:
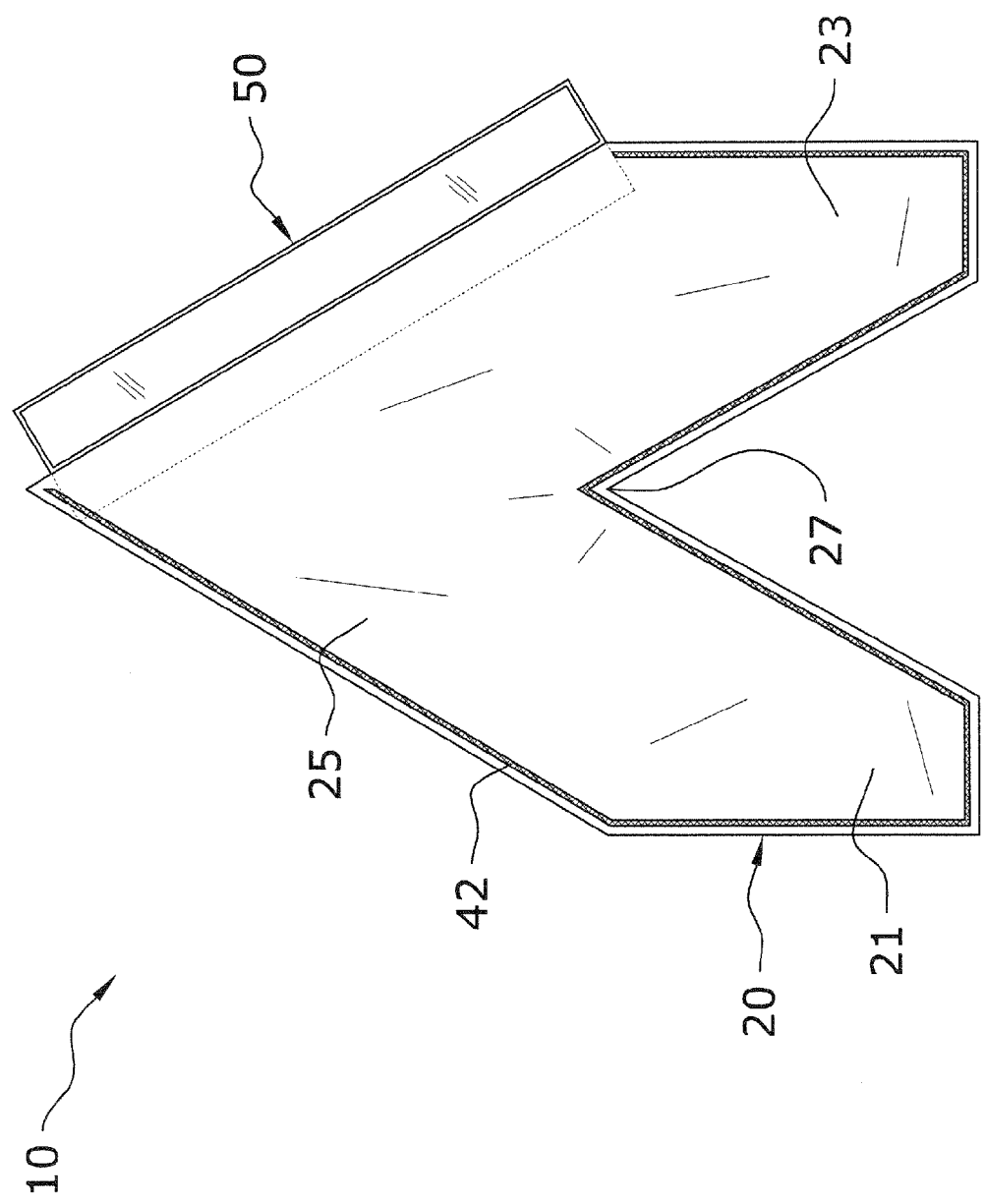
FIG. 12 is a front view of a second alternative embodiment of the present invention.
Figure 13:
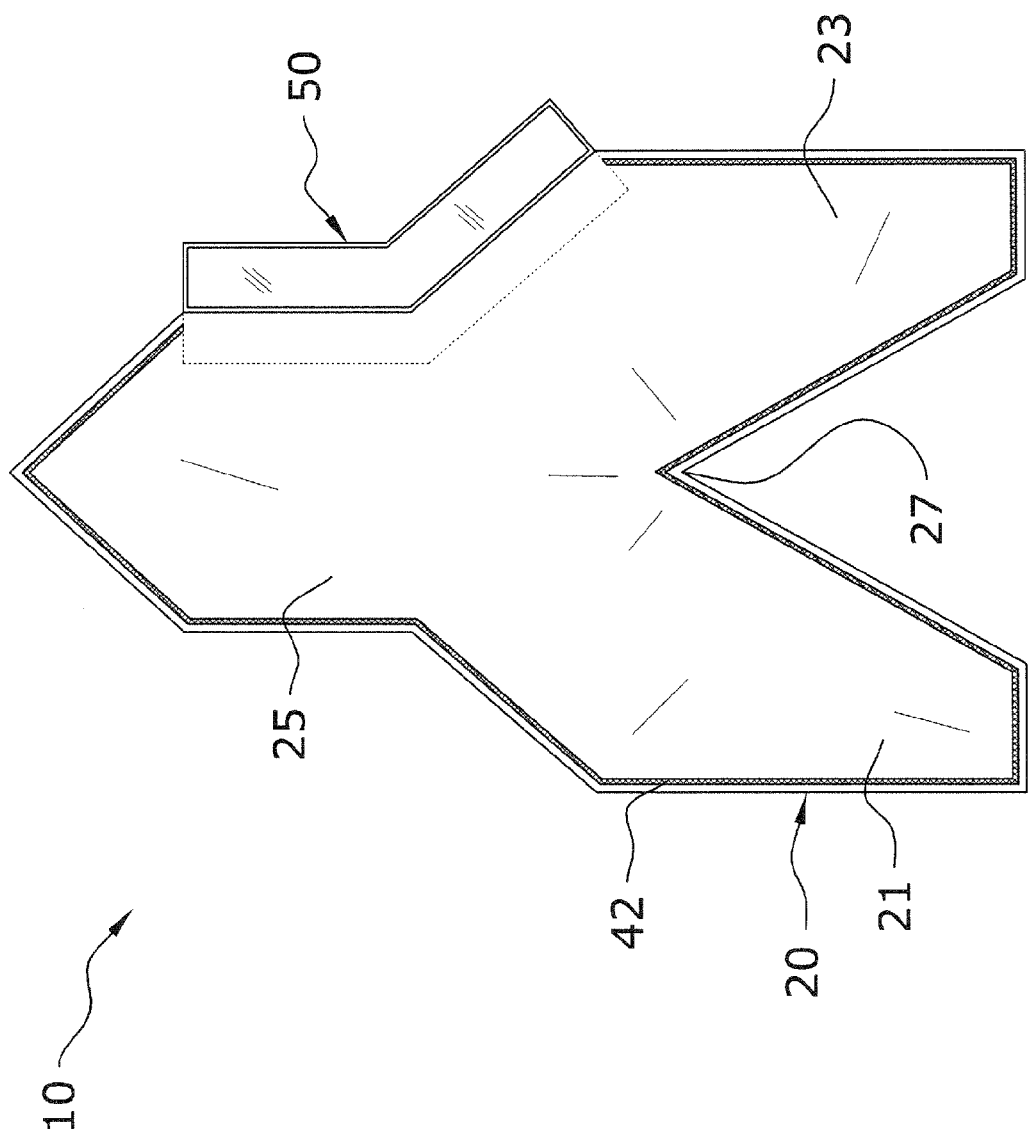
FIG. 13 is a front view of a third alternative embodiment of the present invention.

A second example of a way to manufacture the present invention is illustrated in FIGS. 9 and 10. A quadrilateral shaped hole is first cut through a substantial center of the sheet as illustrated by the cutting line 60 in FIG. 9. The sheet is preferably comprised of a pouch 20 material. The quadrilateral shaped hole is preferably cut, wherein each opposing corner perpendicularly faces an outer edge of the sheet as illustrated in FIG. 9. The quadrilateral shaped hole is then removed from the sheet, thus forming a hole in the center of the sheet. The sheet is then folded in the middle as illustrated by the folding line 61 in FIG. 9. The opposing ends of the sheet are thus joined and form a pouch 20 as shown in FIG. 10. The pouch 20 may then be sealed around the outer perimeter of the pouch 20. An opening 29 is also preferably left unsealed to allow insertion of a medical instrument 12. It is appreciated that the present invention may be manufactured in a plurality of manners other than the described manners above.

In use, the medical instrument 12 (i.e. surgical pliers) is first inserted within the pouch 20 by inserting the handles or legs of the medical instrument 12. Each respective leg is inserted within the respective lower portion 21, 23 of the pouch 20 and the head of the medical instrument 12 is inserted within the upper portion 25 of the pouch 20. When the medical instrument 12 is adequately positioned within the sealed pouch 20 the medical instrument 12 may be sterilized via various techniques, such as but not limited to steam sterilization. It is appreciated that the medical instrument 12 may be sterilized in a plurality of manners and also before insertion into the pouch 20.

The outer layer 58 of the flap 50 is then removed thus revealing the sealing member 56. The second flange portion 54 is then folded over the opening 29 of the pouch 20 and the sealing member 56 is attached to the upper surface of the first layer 30 thus sealing the medical instrument 12 within the pouch 20. The medical instrument 12 may now be positioned upon the respective tool rack 14 (i.e. pliers rack). When the user is ready to utilize the medical instrument 12 the above process is simply reversed. The sealed pouch 20 can also be opened by utilizing a scissors to cut open the pouch 20. In addition, a slit 44 anywhere along the non-sealed periphery of the pouch 20, as shown in FIG. 2, would allow the operator to tear open the pouch 20 with their fingers.

An improved embodiment of the present invention 110 is illustrated in FIGS. 18 through 25, wherein the generally transparent pouch 120 having the inner space 121 similarly has an upper portion 123 with a sealable upper opening 124, a first lower portion 125 extending from the upper portion 123, and a second lower portion 126 extending from the upper portion 123, wherein the inner space 121 extends within the upper portion 123, the first lower portion 125 and the second lower portion 126. The first lower portion 125 and the second lower portion 126 are separated via a cut-out portion 128 (i.e. recessed portion, lower opening) extending between the first lower portion 125 and the second lower portion 126 and fluidly separating the first lower portion 125 from the second lower portion 126. The cut-out portion 128 may include a receiver part 129, such as an enlarged circular opening near an upper end of the cut-out portion 128 for receiving a hanger, such as present upon a tool rack 118, for stabilizing the pouch 120 while on the tool rack 118 or other hanger.

Figure 23:
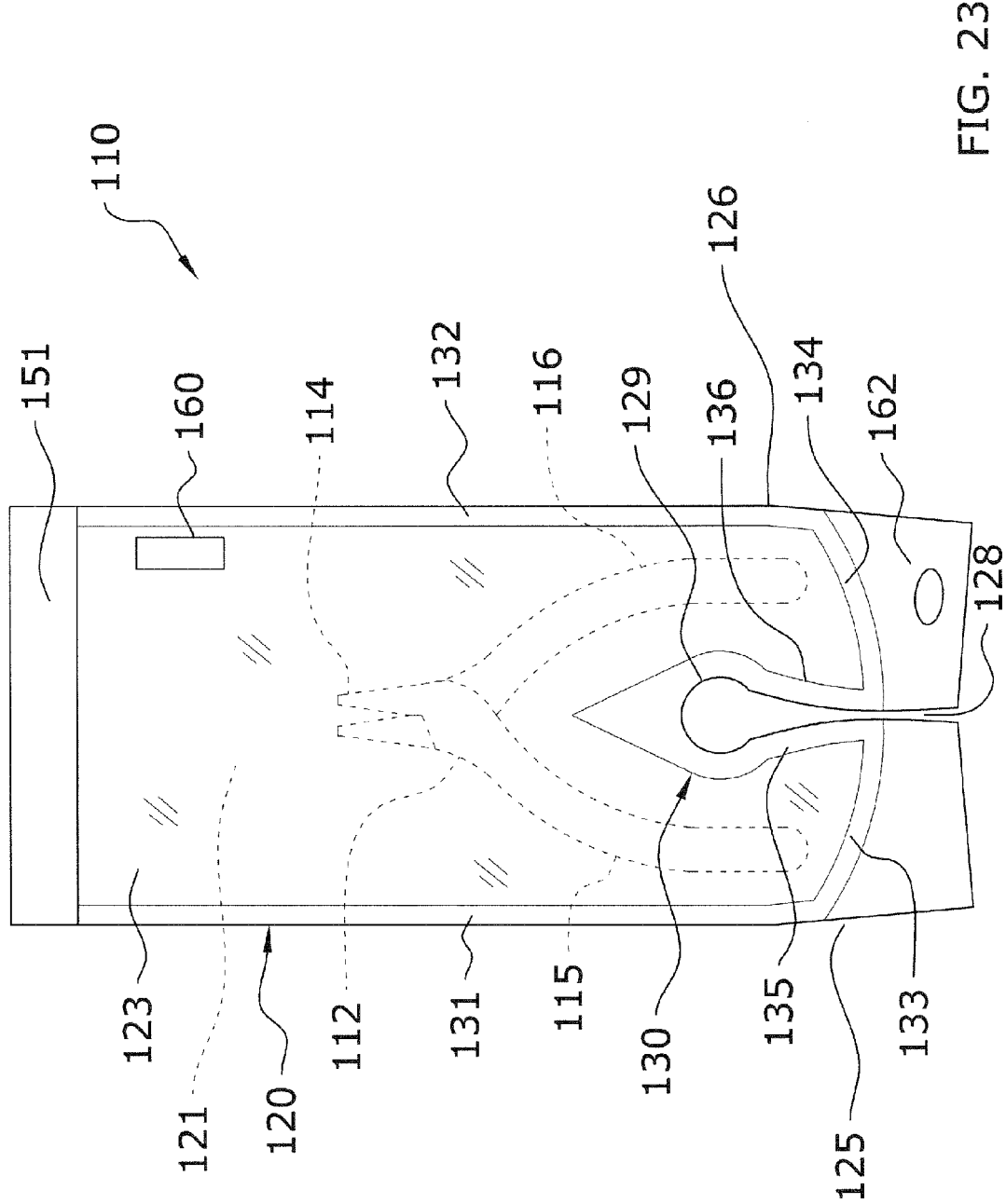
FIG. 23 is a front view of the pliers sealed within the pouch showing the cut-out substantially closed on the lower end.
Figure 24:
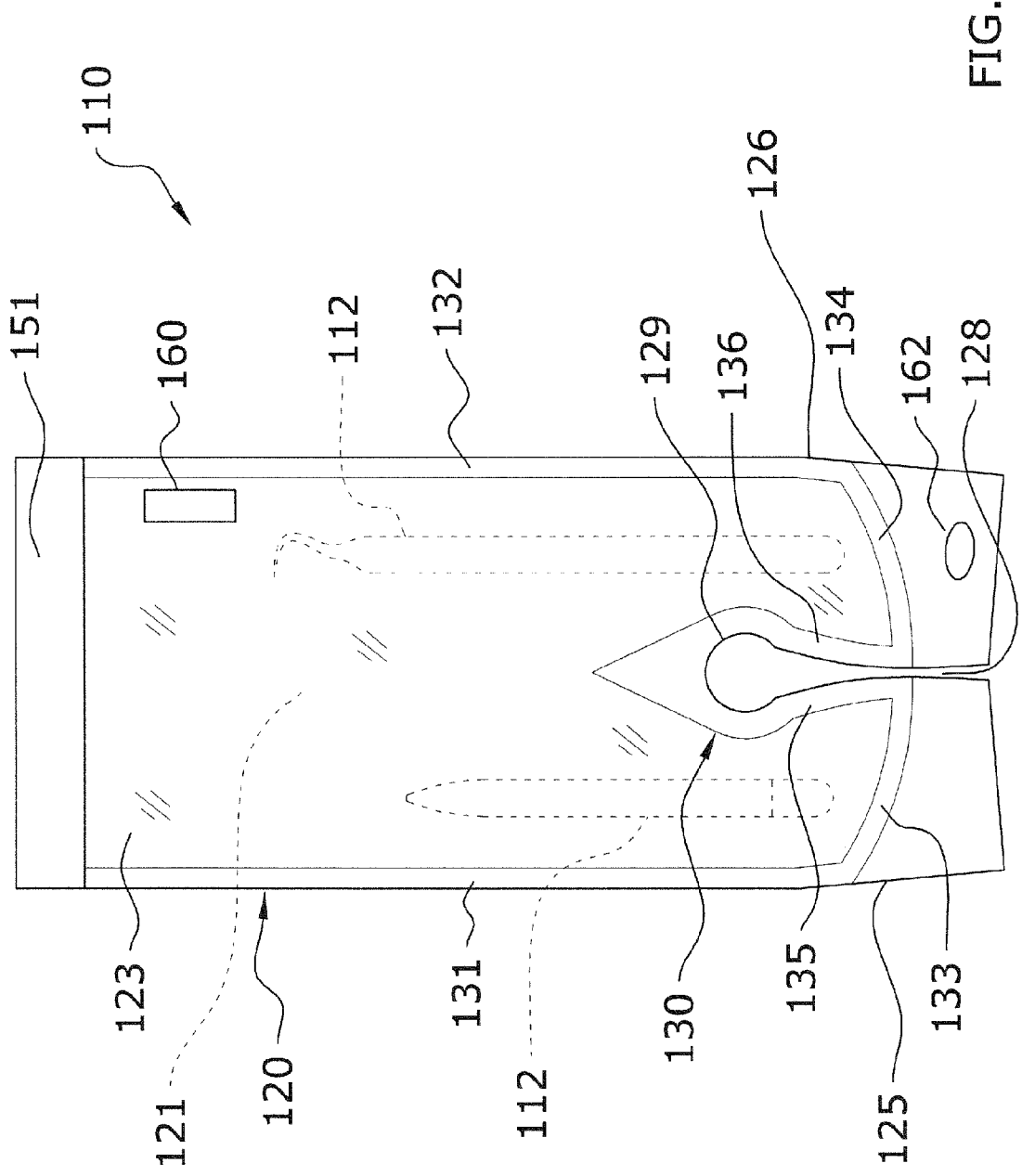
FIG. 24 is a front view of different and multiple medical instruments sealed within the pouch and showing the cut-out substantially closed on the lower end.
Figure 25:
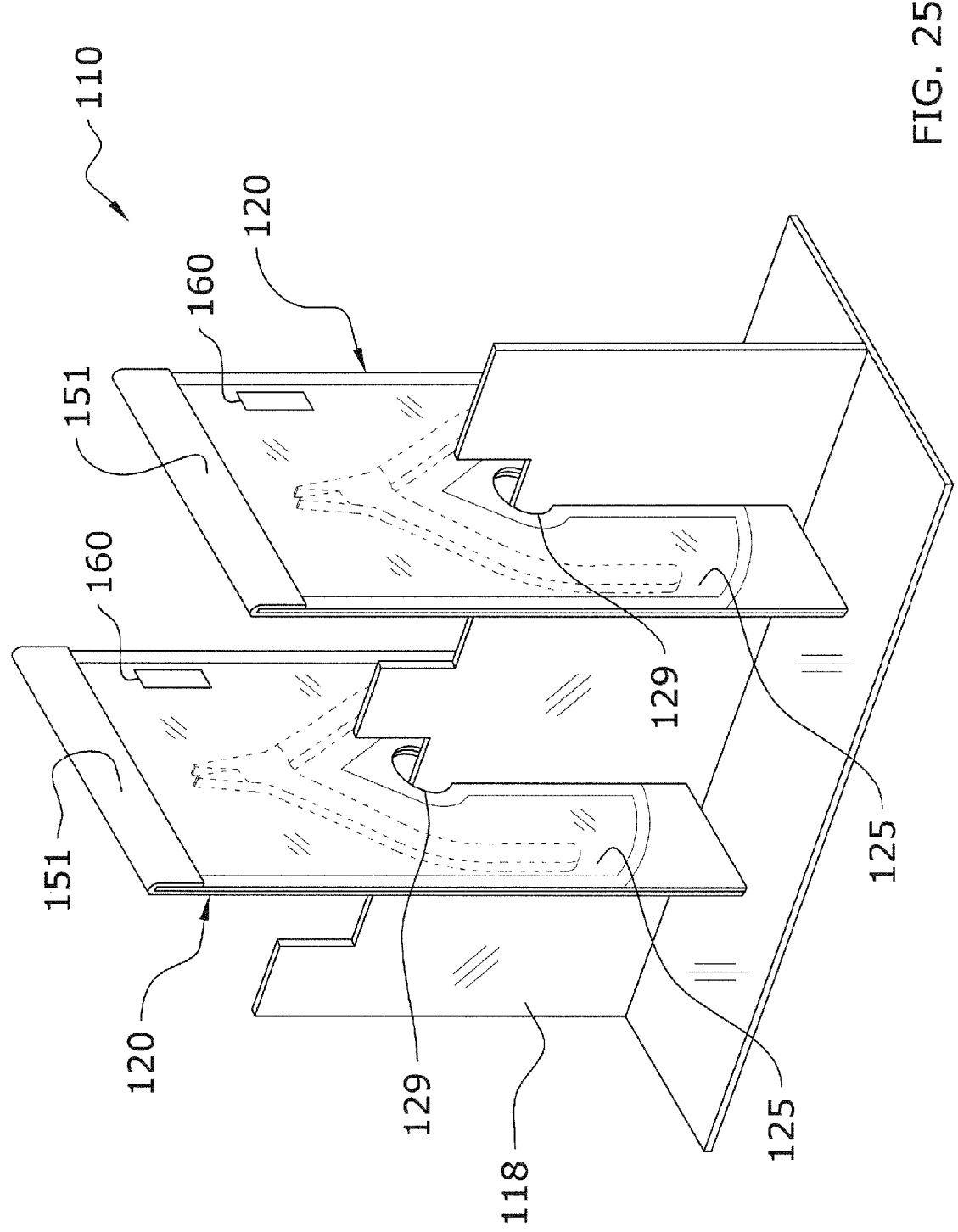
FIG. 25 is an upper perspective view of multiple pouches secured upon a tool rack.

Similarly as before, the inner space 121 receives one or more medical instruments 112, a preferred medical instrument 112 being hinged medical pliers, wherein the head 114 of the pliers is received within the upper portion 123, the first leg 115 is received within the first lower portion 125 and the second leg 116 is received within the second lower portion 126 as exemplarily illustrated in FIGS. 23 and 24. It is appreciated that various other types of medical instruments may be sterilized and contained within the pouch 120, such as but not limited to dental instruments.

The cut-out portion 128 is generally narrow, such as being substantially narrower than the first lower portion 125 and/or the second lower portion 126. One reason for being narrow is to accommodate the tool rack 118, wherein most commercially available racks 118 have a thickness between ⅛ inches and ⅜ inches. By narrowing the cut-out portion 128, there is friction between the lower portions 125, 126 of the pouch 120 and the surface of the racks 118 which increases the retention of the pouches 120 on the rack 118. In addition, the lower portions 125, 126 will fold at an angle when the cut-out portion 128 is narrow allowing the pouches 120 to stand at an angle on rectangular racks 118. The slanted position of the pouches 120 allows easier viewing of the contents and facilitates medical pliers 112 selection. Thus, the cut-out portion 128 preferably has a similar width as the thickness of the hanger of the tool rack 118.

Additionally, the narrower cut-out portion 128 is essential to facilitate aseptic opening of the pouch 120. The first lower portion 125 and the second lower portion 126 should not be apart more than the width of a thumb (the cut-out portion 128 narrower than the width of a thumb), otherwise peeling apart the first layer 140 from the second layer 150 becomes difficult or even improbable for the operator without ripping or tearing the first layer 140 and/or the second layer 150, which will prevent aseptic delivery.

In the new embodiment, the upper portion 123 (above the cut-out portion 128) is vertically elongated, as well as the first lower portion 125 and the second lower portion 126 being vertically elongated; however the upper portion 123 is equal in length or at least as long and preferably longer in length than the first lower portion 125 and the second lower portion 126 as illustrated in FIGS. 23 and 24. The elongated structure of the upper portion 123, the first lower portion 125, and the second lower portion 126 allow for the medical pliers 112 to be held in an open position during sterilization while within the inner space 121 and also to allow the enclosed medical pliers 112 to be placed on a tool rack 118 thus allowing for a more complete sterilization process.

The length of the upper portion 123 being equal or longer than the first lower portion 125 and/or the second lower portion 126 is essential for various reasons; with one reason being that the upper portion 123 must adequately receive the entire head 114 of the medical pliers 112. Additionally, there has to be sufficient clearance upon the upper portion 123 when the upper flap 151 is folded over and sealed upon the first layer 140 so that the upper flap 151 does not cover the head 114 of the medical pliers 112, wherein the pliers 112 are often identified by operators via the shape of the head 114. Additionally, the elongated structure of the upper portion 123 allows for more space between the pliers 112 and the chemical indicator 160 as will be described.

Further, the elongated upper portion 123 is important to facilitate proper aseptic opening of the pouch 120 at the non-sealed extremities (lower flaps 141, 151) of the pouch 120. When the operator grasps the lower flaps 141, 151 to peel apart the first layer 140 and the second layer 150 for accessing the medical pliers 112, the pliers 112 must be able to move towards the upper flap 151 so as to distance the first leg 115 and the second leg 116 of the pliers 112 from the first lower portion 125 and the second lower portion 126 so as not to interfere with the grasping of the lower flaps 141, 151 and opening of the pouch 120.

A seal 130, such as a heat seal, defines the inner chamber and seals the medical instrument 112 within the defined inner space 121 (via the seal 130) in a manner to permit the medical instrument 112 to be sterilized and prevent exterior microorganisms or contaminants from entering the inner space 121. The seal 130 is detachable meaning the first plastic film layer 140 is adhered to the second paper layer 150 by heating an element and stamping the two layers 140, 150 together under pressure, thus forming the seal 130. The adhesion force of the seal 130 is not strong enough to tear the first layer 140 and/or second layer 150 when pulled apart.

The seal 130 generally includes a first side edge 131 extending along the first peripheral side of the pouch 120, a second side edge 132 extending along the second peripheral side of the pouch 120, a first bottom edge 133 extending along the bottom edge of the first lower portion 125, a second bottom edge 134 extending along the bottom edge of the second lower portion 126, a first inner edge 135 extending along the inner peripheral edge of the first lower portion 125 adjacent a first side of the cut-out portion 128, and a second inner edge 136 extending along the inner peripheral edge of the second lower portion 126 adjacent a second side of the cut-out portion 128. It is appreciated that the first inner edge 135 and second inner edge 136 of the heat seal 130 may substantially or entirely close the bottom of the cut-out portion 128 as illustrated in FIGS. 23 and 24 or be separated such as to leave the bottom of the cut-out portion 128 open as illustrated in FIG. 18 through 22.

Figure 18:
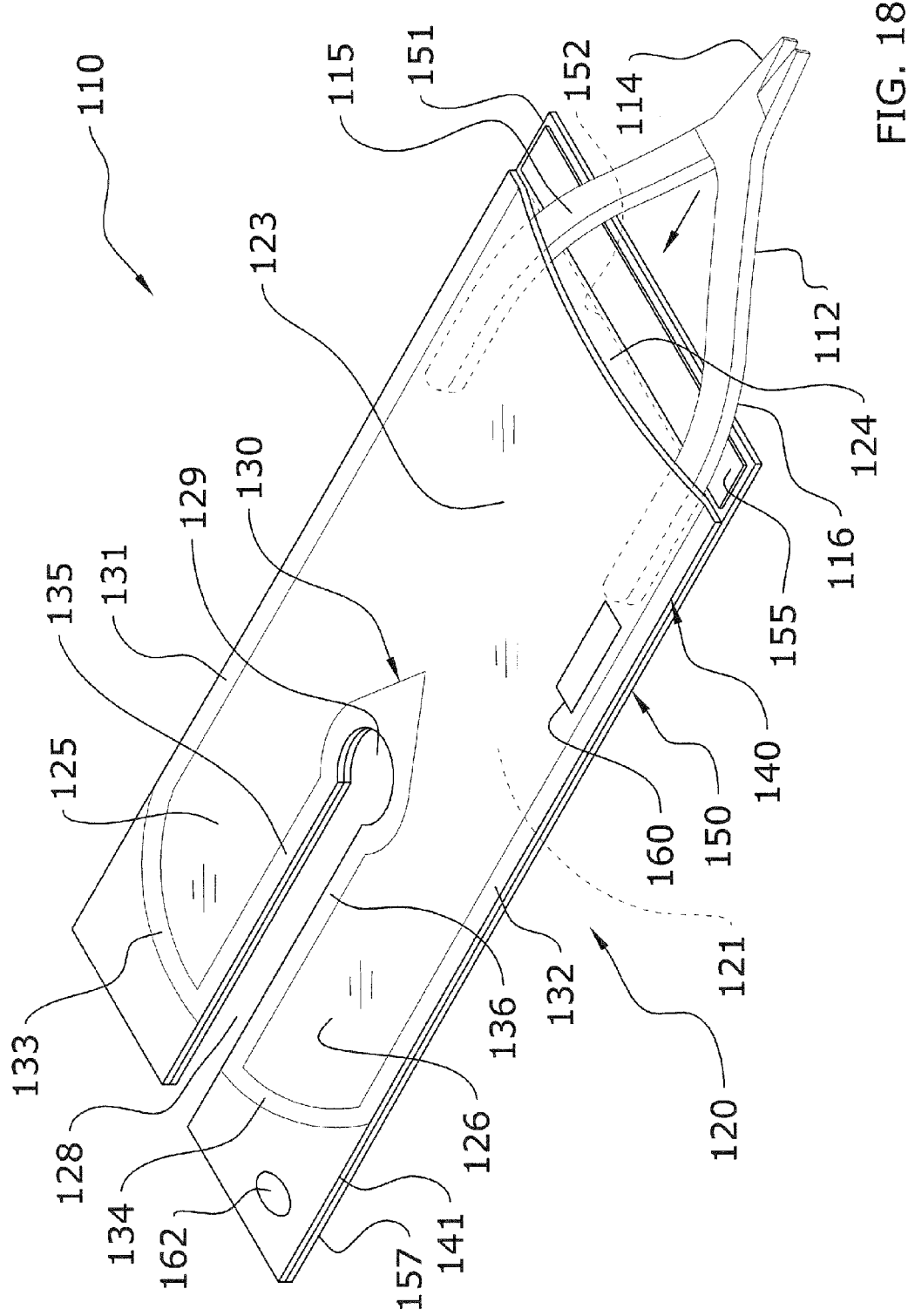
FIG. 18 is an upper perspective view of the new embodiment with the medical pliers being inserted within the inner space through the upper opening.
Figure 19:
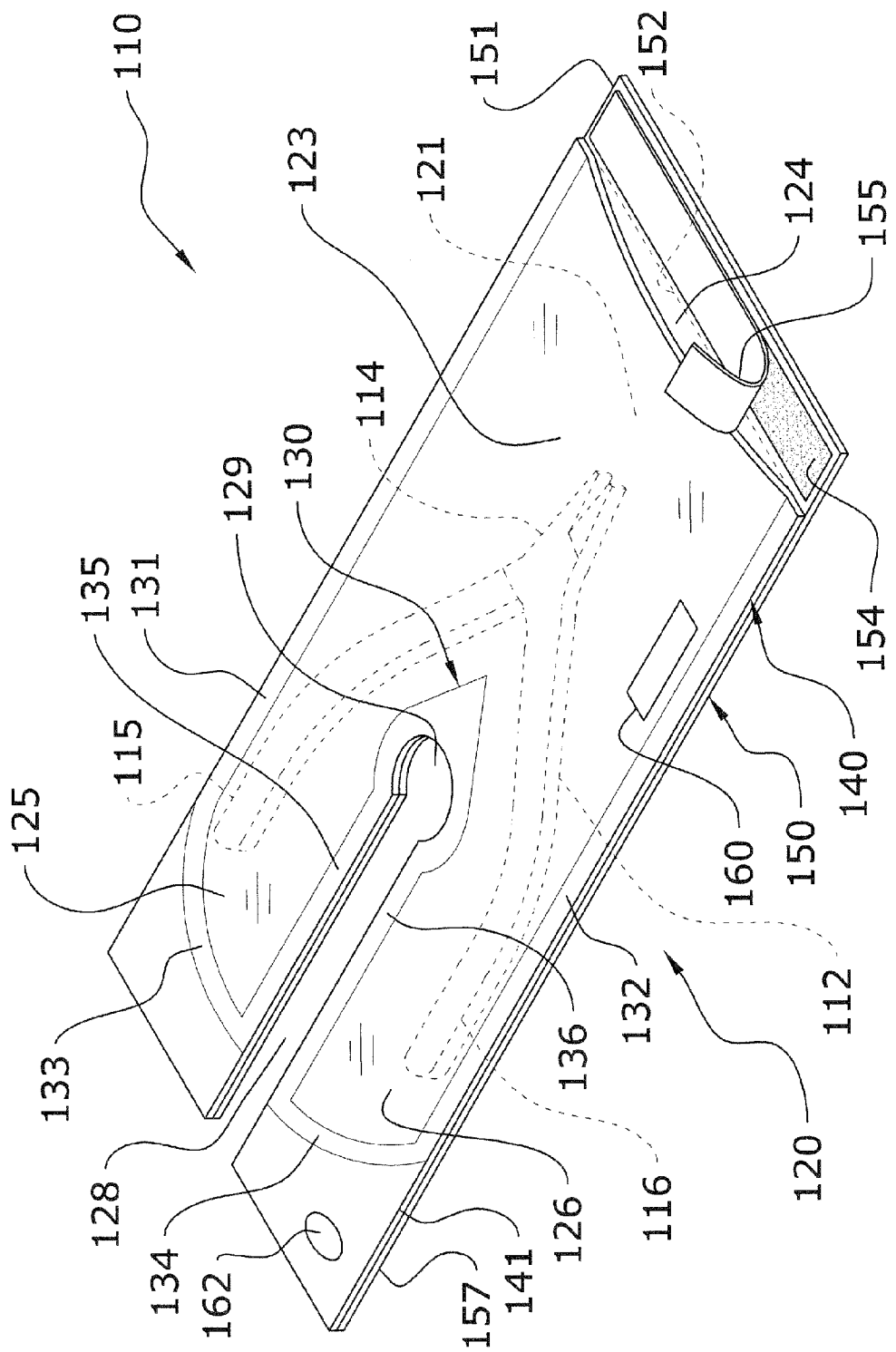
FIG. 19 is an upper perspective view of the new embodiment with the medical pliers inserted within the inner space and the adhesive of the upper flap being exposed.
Figure 20:
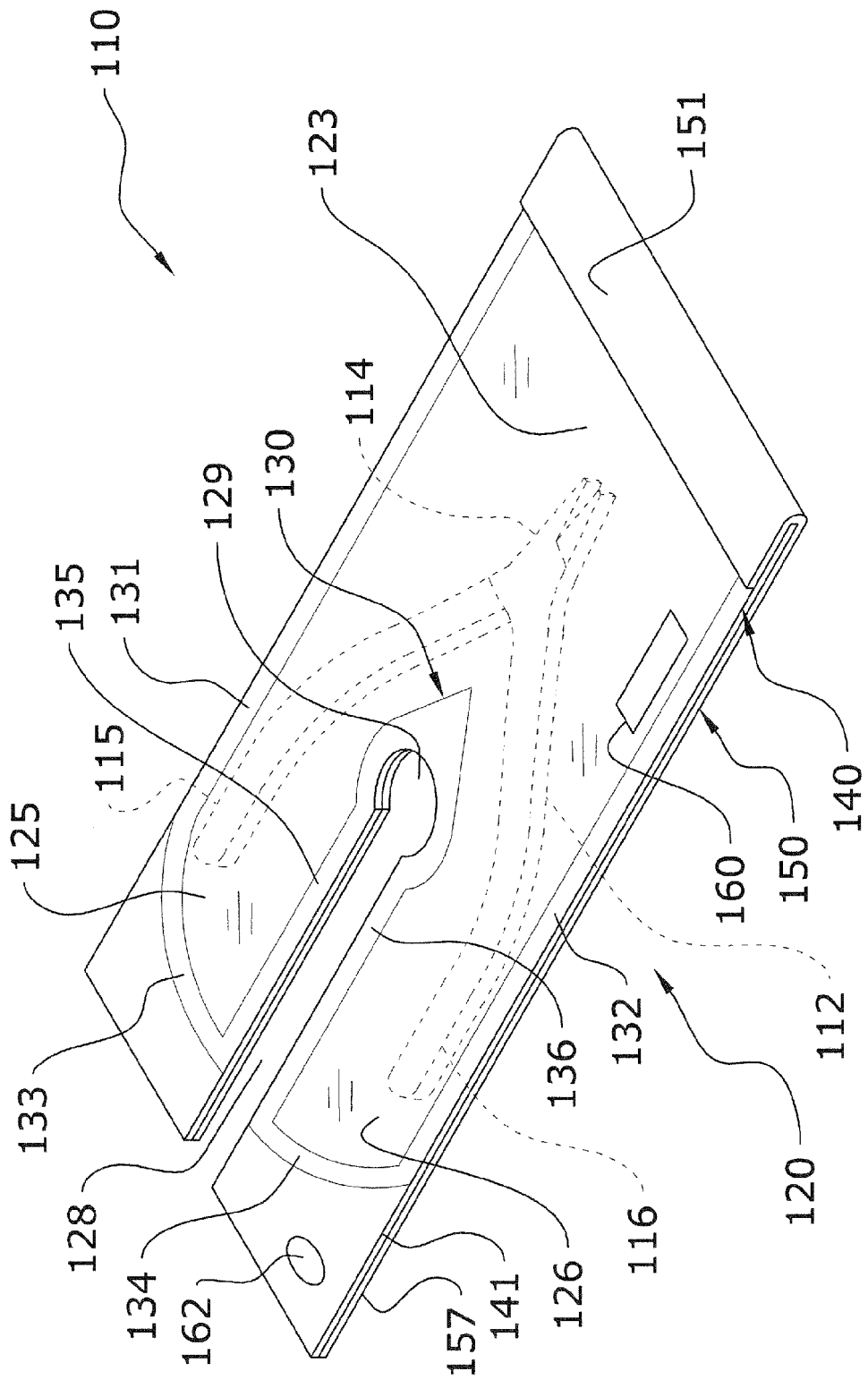
FIG. 20 is an upper perspective view of the new embodiment with the medical pliers inserted within the inner space the upper flap folded over to seal the upper opening and inner space.

The top edge of the pouch 120 is generally left open via the upper opening 124 for inserting the medical instrument 112 within the pouch 120 and sealed after insertion via an upper flap 151 as illustrated in FIGS. 18 through 20. It is appreciated that the upper opening 124 may be located at various places along the upper portion 123 all which allow for the rigid medical pliers 112 or other instrument to be inserted within the inner space 121, thus the upper opening 124 being large enough to receive the medical pliers 112, wherein pliers 112 have a rigid framework and do not permit flexibility when inserting the pliers 112 within the inner space 121 through the upper opening 124. Further, the upper opening 124 generally extends completely across the upper portion 123 (generally minus the first side edge 131 and the second side edge 132 of the seal 130) and is just as wide as the combined width of the first lower portion 125, the cut-out portion 128, and the second lower portion 126 (generally minus the first side edge 131 and the second side edge 132 of the seal 130), thus being of a length substantially similar as the width of the pouch 120.

The pouch 120 is formed via the first layer 140 and the second layer 150 adhered together via the seal 130. The first layer 140 and the second layer 150 are generally comprised of a similar sizes and shapes, generally with the exception of the upper flap 151 of the second layer 150 as will be described. The first layer 140 generally includes a first lower flap 141 integral therewith and the second layer 150 includes a second lower flap 157 integral therewith as illustrated in FIGS. 18 through 22. The first lower flap 141 and the second lower flap 157 may be divided each into a pair of flaps, such as one portion of the first lower flap 141 aligning with the first lower portion 125 and another portion aligning with the second lower portion 126, and likewise for the second lower flap 157. The separation may be formed from the cut-out portion 128 or a separate slit.

The first lower flap 141 and the second lower flap 157 each extend below the first bottom edge 133 and the second bottom edge 134 of the seal 130, thus being removed from the inner space 121 and not directly connected to each other and inwardly spacing the seal 130 from the lowermost edge of the layers 140, 150. The first lower flap 141 and the second lower flap 157 are left separate for opening the pouch 120 to access the sterilized medical instrument 112 and thus peeling the first layer 140 apart from the second layer 150. The seal 130 allows for the first layer 140 and the second layer 150 to be peeled apart without tearing, thus allowing for aseptic delivery of the medical pliers 112 or other instrument from the pouch 120. The layers 140, 150 may be comprised of various materials, such as but not limited to a transparent plastic first layer 140 and a paper second layer 150.

The second layer 150 also generally includes an upper flap 151 to seal the upper opening 124 of the upper portion 123 as illustrated in FIGS. 18 through 20. The upper flap 151 of the second layer 150 generally extends upwardly beyond the first layer 140. The upper flap 151 includes a fold line or perforation 152 also above the upper opening 124 and first layer 140 for folding the upper flap 151. The upper flap 151 also includes a seal 154, such as adhesive upon thereof and which may include a removable covering 155, which when the upper flap 151 is folded downwards adheres to the exterior of the first layer 140 thus sealing the upper opening 124.

The first layer 140 and/or the second layer 150 also preferably include a visible chemical indicator 160 to indicate to the user whether the contents of the pouch 120 within the inner space 121 have been sterilized. The indicator 160 may visually indicate sterilization via various methods, such as but not limited to changing color when the contents (e.g. medical pliers 112) are sterilized. The indicator 160 is generally located upon the upper portion 123 near an upper corner that is adequately spaced from the medical instrument 112 within the inner space 121 to prevent contact of the indicator 160 with the medical instrument 112 such as to prevent the pliers 112 from affecting the indicator 160 and to prevent pollution of the medical instrument 112 with ink and other chemicals from the indicator 160. Also, by locating the indicator 160 upon the upper portion 123, the indicator 160 is ensured to be visible while upon a tool rack 118. The size of the upper portion 123, first lower portion 125, and second lower portion 126 prevent the medical pliers 112 from moving sideways within the inner space 121 thus preventing disturbance of the indicator 160. One of the lower flaps 141, 157 may also include a guide 162 for indicating to the operator the state of the indicator 160, such as by showing and labeling a first color that the indicator 160 would comprise in a non sterilized inner space 121 state and by showing and labeling a second color that the indicator 160 would comprise in a sterilized inner space 121 state.

In use, the medical instrument 112, such as surgical pliers, is first inserted within the pouch 120 by inserting the legs 115, 116 of the medical instrument 112 through the upper opening 124 and following by inserting the head 114 through the upper opening 124 as illustrated in FIGS. 18 and 19. Each respective leg 115, 116 is inserted within the respective lower portion 125, 126, of the pouch 120 and the head 114 of the medical instrument 112 is inserted within the upper portion 123 of the pouch 120. When the medical instrument 112 is adequately positioned within the pouch 120 and the upper opening 124 sealed via the upper flap 151, the medical instrument 112 may be sterilized via various techniques, such as but not limited to steam sterilization. It is appreciated that the medical instrument 112 may be sterilized in a plurality of manners and also before insertion into the pouch 120. The medical instrument 112 may now be positioned upon the respective tool rack 118 (i.e. pliers rack).

Figure 21:
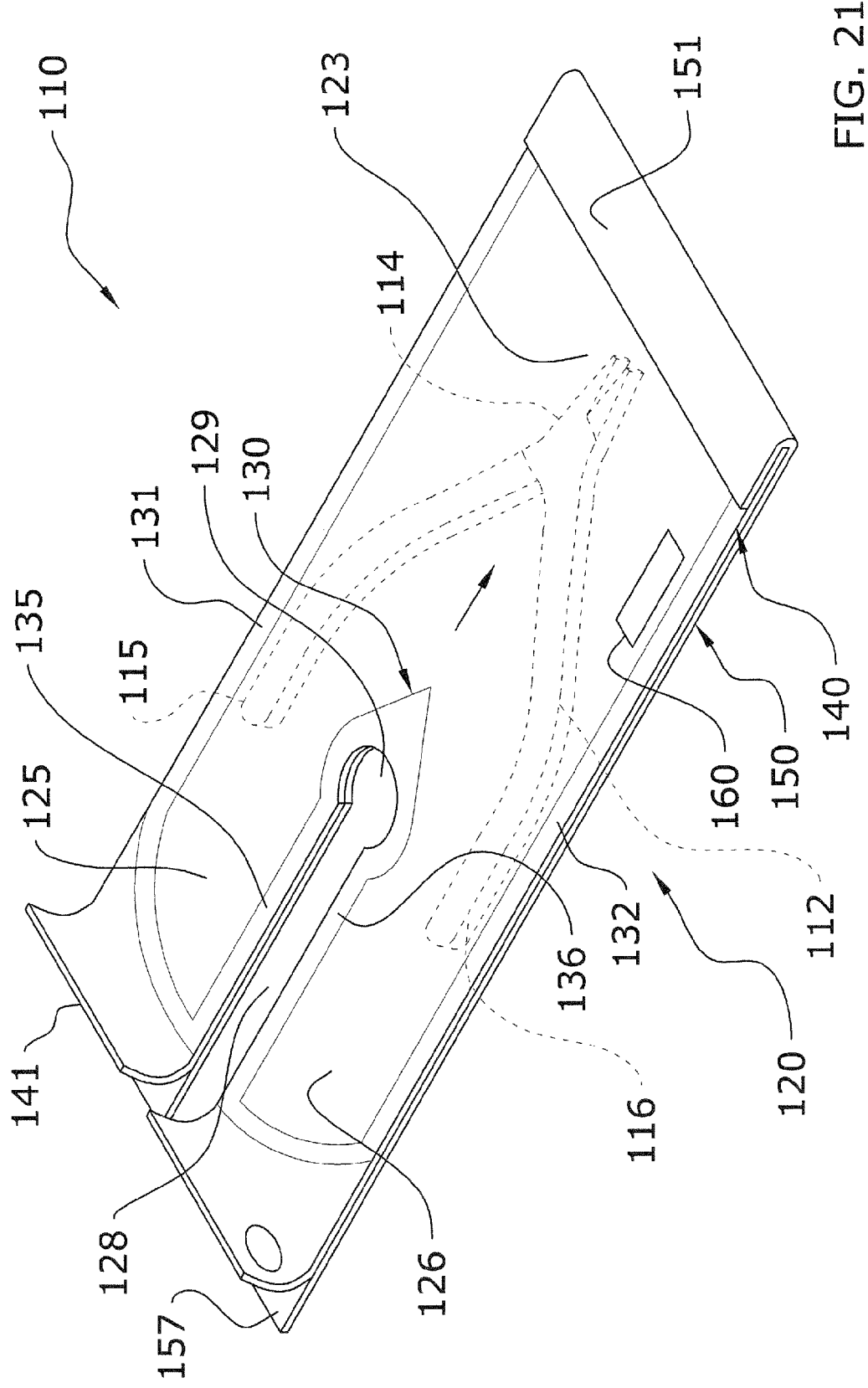
FIG. 21 is an upper perspective view of the new embodiment with the medical pliers inserted within the inner space and the lower flaps peeled apart to move the pliers forwardly towards the upper flap and begin extraction of the pliers from the pouch.
Figure 22:
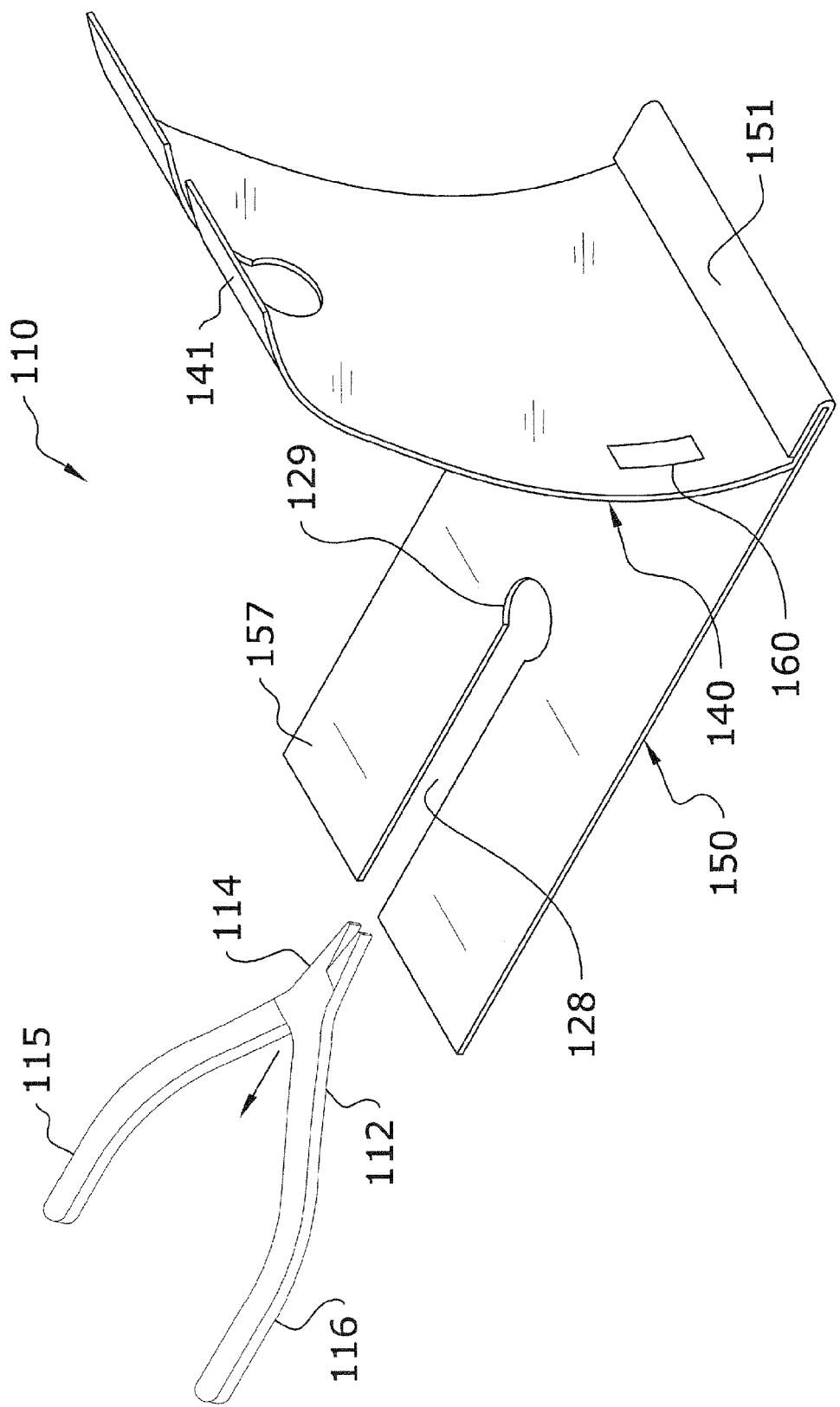
FIG. 22 is an upper perspective view of the new embodiment with the first layer peeled away from the second layer thus permitting aseptic delivery of the pliers from the pouch.

When removing the medical instrument 112 from the pouch 120, the operator grasps the lower flaps 141, 157 of the first layer 140 and the second layer 150 and below the first lower portion 125 and the second lower portion 126. During this step the pliers 112 or other medical instrument slides towards the sealed upper opening 124 and upper flap 151 so that the legs 115, 116 of the pliers 112 are moved away from the first lower portion 125 and the second lower portion 126 as illustrated in FIG. 21. While holding the first lower flap 141 and the second lower flap 157 firmly, the operator peels the first layer 140 apart from the second layer 150 thus effectively breaking the seal 130. The first layer 140 is peeled apart from the second layer 150 intact to expose the sterilized medical instruments 112 as illustrated in FIG. 22.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A sterilization pouch having a sealed inner space therein for receiving one or more medical instruments, said sterilization pouch comprising:
   an upper portion;
   a first lower portion extending from said upper portion;
   a second lower portion extending from said upper portion; and
   a cut-out portion separating said first lower portion from said second lower portion, said cut-out portion being below said upper portion, said cut-out portion adapted to permit said inner space to connect said first lower portion and said second lower portion through said upper portion and to restrict said inner space from connecting said first lower portion directly to said second lower portion;
   wherein said upper portion is comprised of a vertical length of equal length of or longer than said first lower portion and wherein said upper portion is comprised of a vertical length of equal length of or longer than said second lower portion.

2. The sterilization pouch of claim 1, wherein said upper portion is comprised of a vertical length longer than said first lower portion and wherein said upper portion is comprised of a vertical length longer than said second lower portion.

3. The sterilization pouch of claim 1, wherein said upper portion includes a sealable upper opening.

4. The sterilization pouch of claim 3, wherein said upper opening extends across said upper portion such as to be a substantially similar width as the upper portion.

5. The sterilization pouch of claim 4, wherein said upper opening is comprised of a length substantially similar to the combined width of the first lower portion, the cut-out portion, and the second lower portion.

6. The sterilization pouch of claim 5, including a flap extending from said upper portion, wherein said flap seals said upper opening.

7. The sterilization pouch of claim 6, wherein said opening and said flap extend along a top edge of said upper portion.

8. The sterilization pouch of claim 7, wherein said opening and said flap are positioned entirely above said cut-out portion.

9. The sterilization pouch of claim 1, wherein said cut-out is substantially narrower relative said first lower portion and wherein said cut-out is substantially narrower relative said second lower portion.

10. The sterilization pouch of claim 1, including a visual indicator upon said upper portion, said visual indicator in fluid contact with said inner space for indicating whether sterilization has occurred within said sealed inner space.

11. A sterilization pouch comprising:
    a first layer and a second layer wherein said first layer is attached to said second layer via a seal, wherein said seal defines an inner space between said first layer and said second layer for receiving one or more medical instruments;
    wherein said seal defines an upper portion, a first lower portion extending from said upper portion, a second lower portion extending from said upper portion, and a cut-out portion;
    wherein said cutout portion is between said first lower portion from said second lower portion, said cut-out portion being below said upper portion, said cut-out portion adapted to permit said inner space to connect said first lower portion and said second lower portion through said upper portion and to restrict said inner space from connecting said first lower portion directly to said second lower portion;
    wherein said upper portion is comprised of a vertical length of equal length of or longer than said first lower portion and wherein said upper portion is comprised of a vertical length of equal length of or longer than said second lower portion.

12. The sterilization pouch of claim 11, wherein said first layer includes a first lower flap below a bottom edge of said seal and wherein said second layer includes a second lower flap below said bottom edge of said seal, said first lower flap and said second lower flap being external to said inner space via said bottom edge of said seal.

13. The sterilization pouch of claim 11, wherein said seal is comprised of a heat formed seal.

14. The sterilization pouch of claim 11, wherein said upper portion includes a sealable upper opening between said first layer and said second layer, wherein said second layer includes an upper flap extending above said first layer for being folded over and sealing said upper opening, said upper flap having an adhesive seal.

15. The sterilization pouch of claim 14, wherein said upper opening and said flap extend across said upper portion such as to be a substantially similar width as the upper portion.

16. The sterilization pouch of claim 15, wherein said upper opening and said flap are comprised of a horizontal length substantially similar to the combined width of the first lower portion, the cut-out portion, and the second lower portion.

17. The sterilization pouch of claim 11, wherein said upper portion is comprised of a vertical length longer than said first lower portion and wherein said upper portion is comprised of a vertical length longer than said second lower portion.

18. The sterilization pouch of claim 11, wherein said cut-out is substantially narrower relative said first lower portion and wherein said cut-out is substantially narrower relative said second lower portion.

19. The sterilization pouch of claim 11, including a visual indicator upon said upper portion of said first layer or said second layer, said visual indicator in fluid contact with said inner space for indicating whether sterilization has occurred within said sealed inner space.

20. A pliers and sterilization pouch, comprising:
a hinged pliers, said pliers having a working head, a first leg, and a second leg, each of said legs extending from said working head in a hinged manner; and
a pouch having an inner space to extend within an upper portion, a first lower portion, and a second lower portion of said pouch, said upper portion receives said working head, said first lower portion receives said first leg, and said second lower portion receives said second leg;
wherein said pouch includes a cut-out portion separating said first lower portion from said second lower portion, said cut-out portion being below said upper portion, said cut-out portion adapted to permit said inner space to connect said first lower portion and said second lower portion through said upper portion and to restrict said inner space from connecting said first lower portion directly to said second lower portion;
wherein said upper portion is above said cut-out portion and wherein said upper portion is comprised of a vertical length of equal length of or longer than said first lower portion and wherein said upper portion is comprised of a vertical length of equal length of or longer than said second lower portion.

* * * * *